United States Patent
DelGiacco et al.

(10) Patent No.: US 9,427,512 B2
(45) Date of Patent: *Aug. 30, 2016

(54) FILTER DEVICE

(75) Inventors: Gerard R. DelGiacco, Yonkers, NY (US); Paxton E. Provitera, East Meadow, NY (US)

(73) Assignee: Pall Corporation, Port Washington, NY (US)

( * ) Notice: Subject to any disclaimer, the term of this patent is extended or adjusted under 35 U.S.C. 154(b) by 684 days.

This patent is subject to a terminal disclaimer.

(21) Appl. No.: 13/491,852

(22) Filed: Jun. 8, 2012

(65) Prior Publication Data

US 2013/0327712 A1 Dec. 12, 2013

(51) Int. Cl.
*A61M 1/36* (2006.01)
*A61M 5/165* (2006.01)
*A61M 1/34* (2006.01)

(52) U.S. Cl.
CPC .......... *A61M 1/3633* (2013.01); *A61M 1/3635* (2014.02); *A61M 5/165* (2013.01); *A61M 1/3496* (2013.01); *A61M 2202/0439* (2013.01)

(58) Field of Classification Search
CPC ........... A61M 1/3633; A61M 1/3635; A61M 1/3496; A61M 5/165; A61M 2005/1655; A61M 2202/005; A61M 2202/0413; A61M 2202/0439; B01D 29/0004; B01D 29/0027; B01D 29/0095; B01D 29/01; B01D 29/05; B01D 29/90; B01D 29/92; B01D 39/14; B01D 39/16; B01D 39/1607; B01D 2201/0407; B01D 2201/0415; G01N 30/6017; G01N 30/603

See application file for complete search history.

(56) References Cited

U.S. PATENT DOCUMENTS

| | | | | |
|---|---|---|---|---|
| 2,772,002 A | * | 11/1956 | Mauro | 210/445 |
| 3,202,286 A | * | 8/1965 | Smit | B01D 24/266 210/286 |
| 3,374,606 A | * | 3/1968 | Baddour | G01N 30/38 95/85 |
| 4,092,246 A | | 5/1978 | Kummer | |
| 4,159,954 A | | 7/1979 | Gangemi | |
| 4,375,415 A | | 3/1983 | Lavender | |
| 4,382,808 A | | 5/1983 | Van Wormer, Jr. et al. | |
| 4,450,082 A | * | 5/1984 | Tanouchi | B01D 15/00 210/290 |
| 4,557,830 A | * | 12/1985 | Onitsuka | B01D 15/22 210/198.2 |
| 4,880,548 A | * | 11/1989 | Pall et al. | 210/767 |
| 4,923,620 A | | 5/1990 | Pall | |
| 5,399,265 A | * | 3/1995 | Nehls | 210/490 |
| 5,527,472 A | | 6/1996 | Bellotti et al. | |
| 5,626,751 A | * | 5/1997 | Kikuchi et al. | 210/321.75 |
| 5,690,825 A | * | 11/1997 | Parton | 210/350 |

(Continued)

FOREIGN PATENT DOCUMENTS

CN 2436161 Y 6/2001
EP 0 313 348 A2 4/1989

(Continued)

OTHER PUBLICATIONS

Chinese Application No. 201310223472.9 Office Action, dated Dec. 31, 2014.

(Continued)

*Primary Examiner* — David C Mellon
(74) *Attorney, Agent, or Firm* — Leydig, Voit & Mayer

(57) ABSTRACT

Devices, systems, and methods for obtaining one or more desired fluid components, using a back-flushable filter device comprising a filter and at least one diffusing plate, are disclosed.

15 Claims, 17 Drawing Sheets

(56) References Cited

U.S. PATENT DOCUMENTS

| | | |
|---|---|---|
| 6,268,119 B1 | 7/2001 | Sumita et al. |
| 6,544,751 B1 | 4/2003 | Brandwein et al. |
| 7,291,450 B2 | 11/2007 | Sowemimo-Coker et al. |
| 2005/0247627 A1 | 11/2005 | Bormann et al. |
| 2008/0081033 A1 | 4/2008 | Sowemimo-Coker et al. |
| 2010/0291629 A1 | 11/2010 | Fournier-Wirth et al. |
| 2011/0224645 A1 | 9/2011 | Winqvist et al. |
| 2012/0213754 A1 | 8/2012 | Chapman |

FOREIGN PATENT DOCUMENTS

| | | |
|---|---|---|
| JP | 57-145662 A | 9/1982 |
| JP | 2007-204016 A | 11/2007 |
| JP | 2007-304016 A | 11/2007 |
| JP | 2012-501708 A | 1/2012 |
| WO | WO 94/21124 A1 | 9/1994 |
| WO | WO 98/01207 | 1/1998 |
| WO | WO 2004/033396 A2 | 4/2004 |
| WO | WO 2005/052137 A1 | 6/2005 |
| WO | WO 2005/094914 A1 | 10/2005 |
| WO | WO 2008/005960 A2 | 1/2008 |
| WO | WO 2010/029317 A2 | 3/2010 |

OTHER PUBLICATIONS

Notice of Reasons for Rejection, Japanese Application No. P2013-089391 dated Mar. 4, 2014.

European Search Report, European Application No. 13165119.2, dated Sep. 19, 2013.

State Intellectual Property Office of the People's Republic of China; First Office Action in Chinese Patent Application No. 201310223472.9 dated Jun. 17, 2014.

Singapore Search Report, Singapore Application No. 201302996-2, dated Oct. 15, 2013.

\* cited by examiner

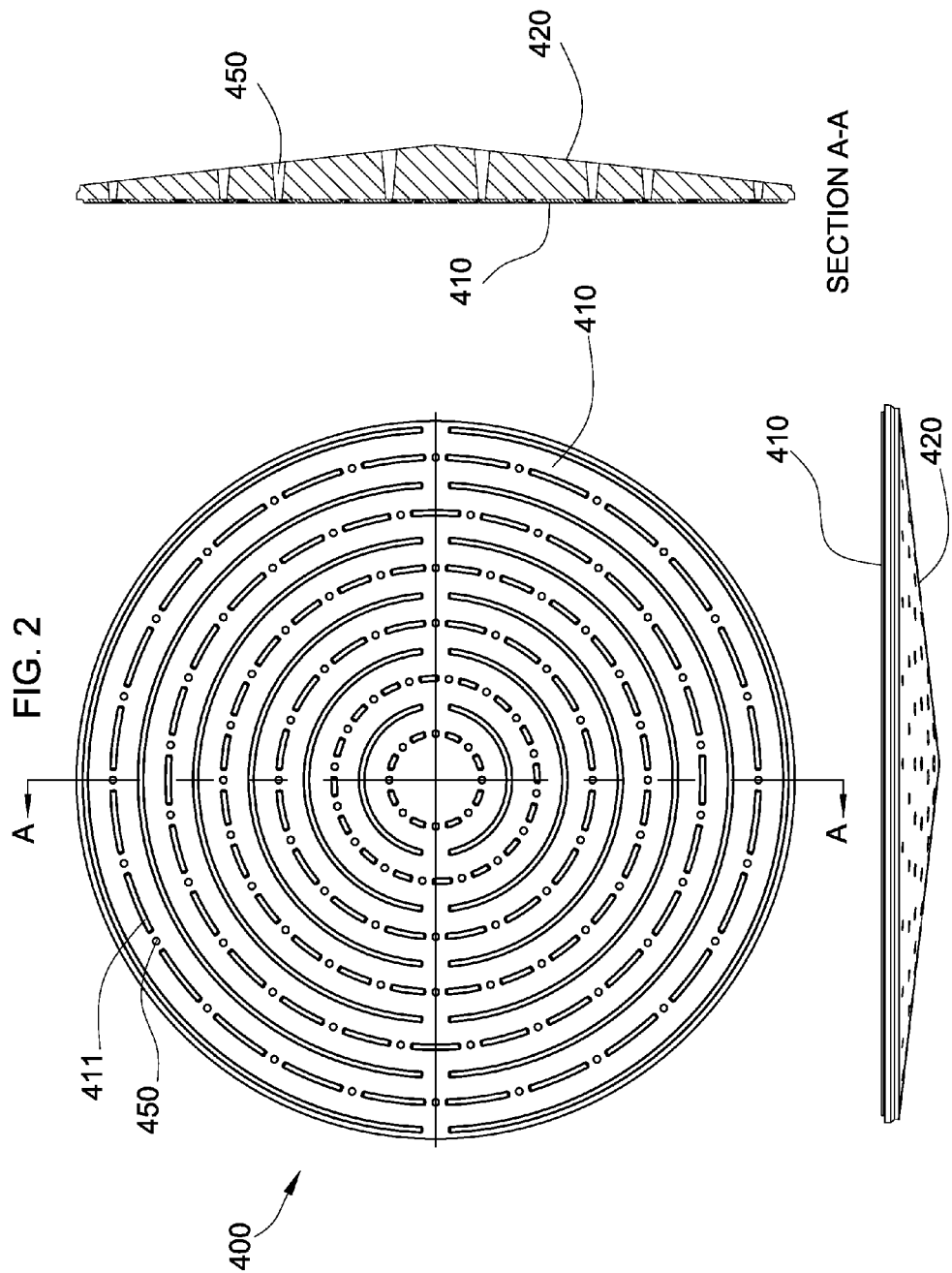

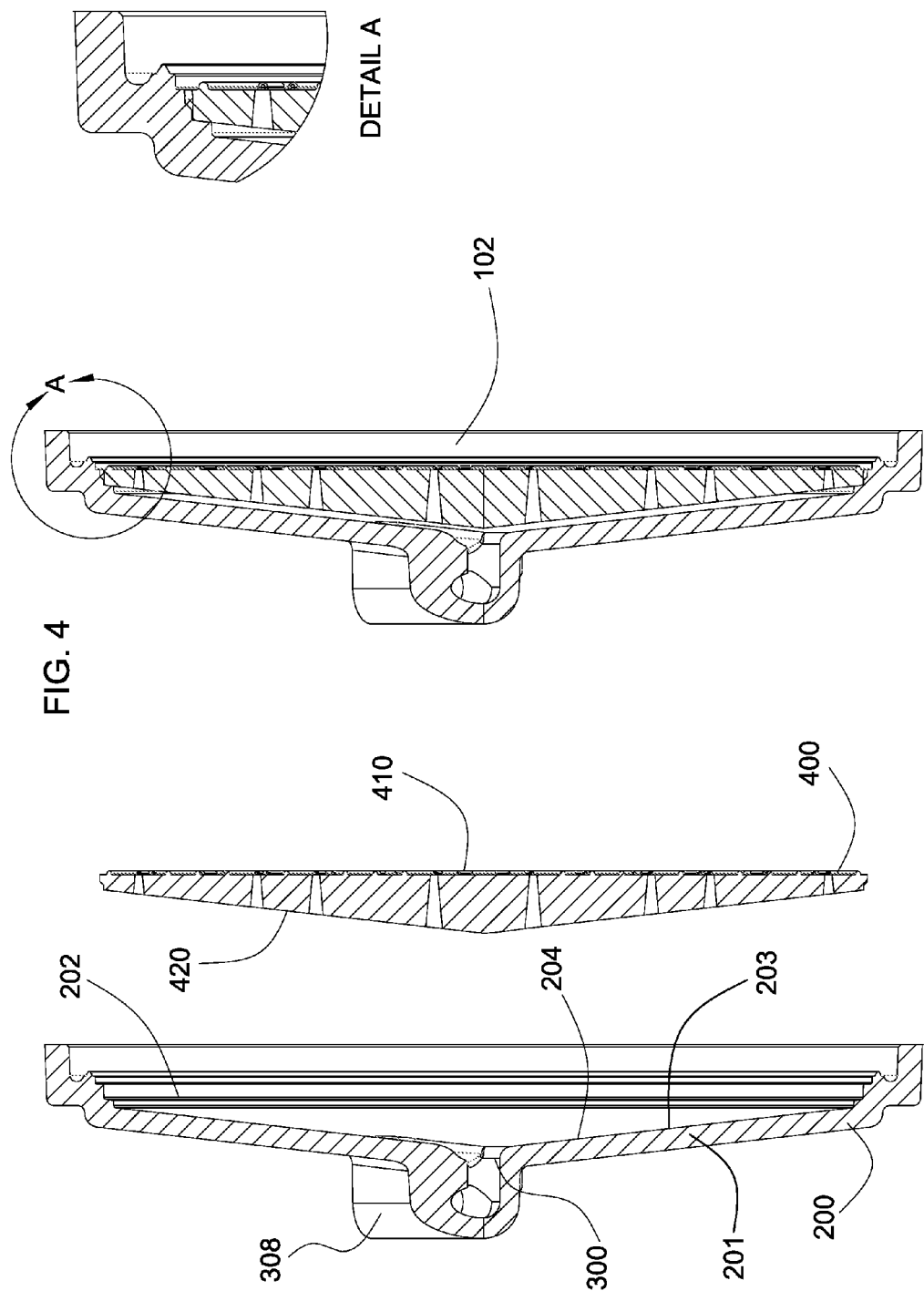

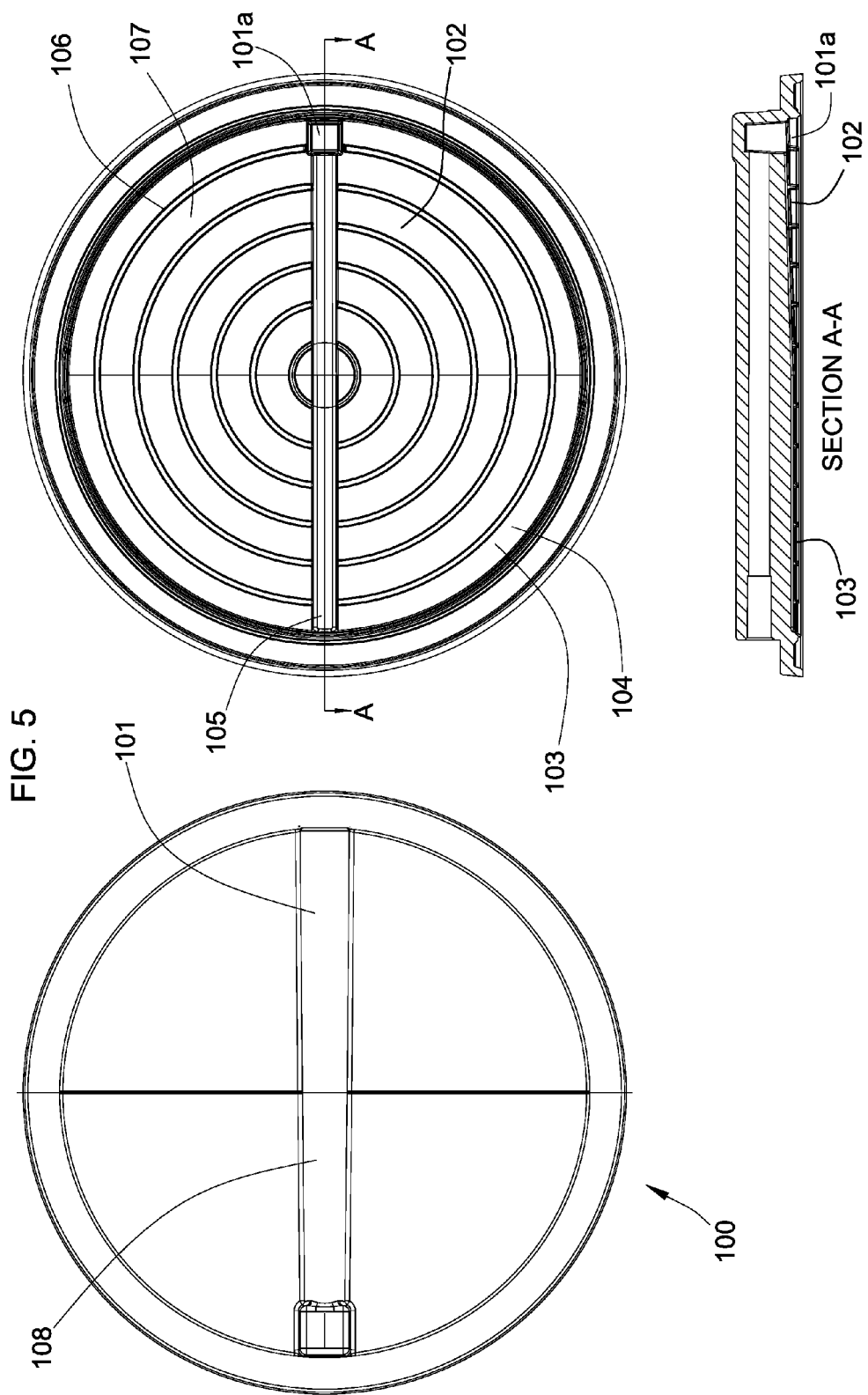

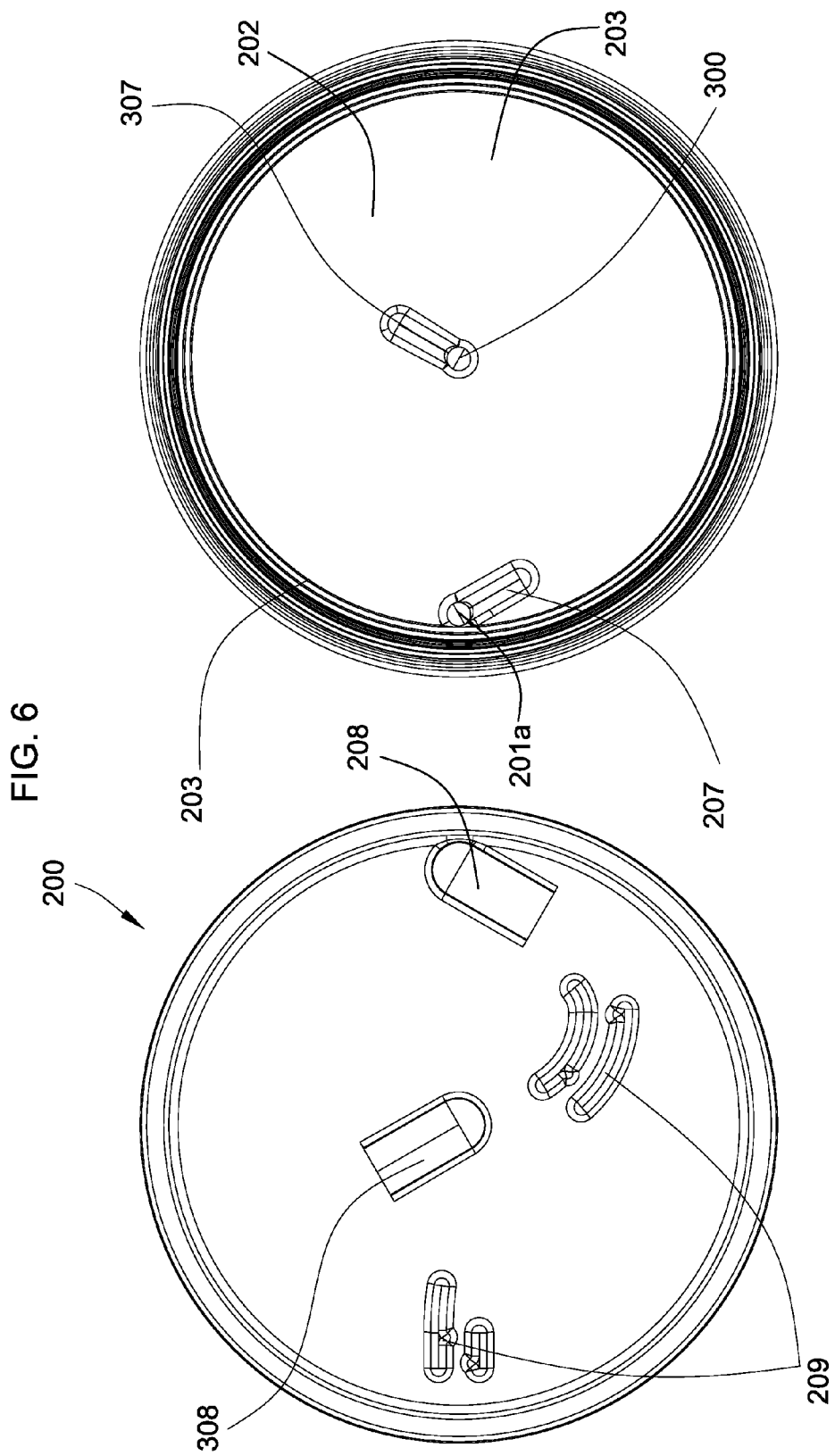

FILTER DEVICE

BACKGROUND OF THE INVENTION

In view of the interest in leukocytes for use in a variety of applications, some methods for harvesting the leukocytes involve passing blood or blood products through commercially available leukocyte depletion filter devices (via the device inlet and through the device outlet) to capture leukocytes by the filter medium in the device housing, and subsequently eluting the leukocytes from the device by passing an elution fluid in the opposite direction through the filter device (via the outlet and through the inlet).

However, there is a need for devices and methods for improving the efficiency of recovery. These and other advantages of the present invention will be apparent from the description as set forth below.

BRIEF SUMMARY OF THE INVENTION

An embodiment of the invention provides a biological fluid processing device comprising (a) a housing comprising an inlet portion including one or more ports, an outlet portion including one or more ports, and defining at least one fluid flow path between an inlet portion port and an outlet portion port, (b) a porous filter having a first surface and a second surface, disposed in the housing across the fluid flow path; and (c) a first perforated diffusing plate having a first surface and a second surface, disposed in the housing across the fluid flow path, wherein the first diffusing plate is disposed in the housing between the second surface of the porous filter and the outlet portion port(s). Preferably, the outlet portion includes a first port comprising an outlet port, and a second port comprising an elution fluid inlet port, and the housing defines a first fluid flow path between an inlet portion port and the outlet port, and a second fluid flow path between an inlet portion port and the elution fluid inlet port. In an embodiment, the inlet portion includes a first port comprising an inlet port, and a second port comprising an elution fluid outlet port, and the housing defines a first fluid flow path between the inlet portion inlet port and the outlet portion outlet port, and a second fluid flow path between the outlet portion elution fluid inlet port and the inlet portion elution fluid inlet port.

In some embodiments, the biological fluid processing device further comprises a second perforated diffusing plate having a first surface and a second surface, disposed in the housing across the fluid flow path(s), wherein the second diffusing plate is disposed in the housing between the first surface of the porous filter and the inlet portion port(s).

Preferably, the porous filter comprises at least one porous leukocyte depletion medium.

Another embodiment of the invention provides a biological fluid processing device comprising (a) a housing comprising an inlet portion including an inlet port, an outlet portion including an outlet port and an elution fluid inlet port, and defining a fluid flow path between the inlet portion inlet port and the outlet portion outlet port, and a fluid flow path between the outlet portion elution fluid inlet port and the inlet portion inlet port; (b) a porous filter having a first surface and a second surface, disposed in the housing across the fluid flow paths; and (c) a first perforated diffusing plate having a first surface and a second surface, disposed in the housing across the fluid flow paths, wherein the diffusing plate is disposed in the housing between the second surface of the porous filter and the outlet portion ports.

Yet another embodiment of the invention provides a biological fluid processing device comprising (a) a housing comprising an inlet portion including at least an inlet port, an outlet portion including an outlet port, and an elution fluid inlet port, and defining a fluid flow path between the inlet portion inlet port and the outlet portion outlet port, and a fluid flow path between the outlet portion elution fluid inlet port and an inlet portion port; (b) a porous filter having a first surface and a second surface, disposed in the housing across the fluid flow paths; (c) a first perforated diffusing plate having a first surface and a second surface, disposed in the housing across the fluid flow paths, wherein the diffusing plate is disposed in the housing between the second surface of the porous filter and the outlet portion ports; and (d) as second perforated diffusing plate having a first surface and a second surface, disposed in the housing across the fluid flow paths, wherein the diffusing plate is disposed in the housing between the first surface of the porous filter and the inlet portion ports. In some embodiments of the device, the inlet portion includes an inlet port and an elution fluid outlet port, and the housing defines a fluid flow path between the inlet portion inlet port and the outlet portion outlet port, and a fluid flow path between the outlet portion elution fluid inlet port and an inlet portion elution fluid outlet port; wherein the porous filter, and first perforated diffusing plate, and the optional second perforated diffusing plate, are disposed in the housing across the fluid flow paths.

In another embodiment, a method for obtaining one or more desired biological fluid components comprises (a) passing a biological fluid through an embodiment of the biological fluid filter device, wherein the fluid passes from an inlet portion port through an outlet portion port, wherein one or more desired biological fluid components are retained by the filter as the fluid passes along a fluid flow path from an inlet portion port through an outlet portion port; b) passing an elution fluid along a fluid flow path from an outlet portion elution fluid inlet port through the first diffusing plate, the filter, and an inlet portion port, wherein the elution fluid elutes one or more desired biological fluid components from the filter; and, obtaining one or more of the eluted desired biological fluid components.

In an embodiment of the method wherein the biological fluid filter device further comprises a second diffusing plate, a method for obtaining one or more desired biological fluid components comprises (a) passing a biological fluid through an embodiment of the biological fluid filter device, wherein the fluid passes from an inlet portion port through an outlet portion port, wherein one or more desired biological fluid components are retained by the filter as the fluid passes along a fluid flow path from an inlet portion port through an outlet portion port; b) passing an elution fluid along a fluid flow path from an outlet portion elution fluid inlet port through the first diffusing plate, the filter, the second diffusing plate, and an inlet portion port, wherein the elution fluid elutes one or more desired biological fluid components from the filter; and, obtaining one or more of the eluted desired biological fluid components.

In another embodiment, a biological fluid processing system is provided, comprising an embodiment of the biological fluid processing device, in fluid communication with at least one container, more preferably, at least two containers. In one embodiment of the system, one of the containers comprises a container suitable for cryopreservation of stem cells and/or leukocytes.

BRIEF DESCRIPTION OF THE SEVERAL VIEWS OF THE DRAWING(S)

FIG. 2 shows perspective, side, and cross-sectional views of an embodiment of a diffusing plate for use in an embodiment of the filter device of the present invention.

FIG. 4 shows a partial cross-sectional view of embodiments of the diffusing plate and the outlet portion of a filter device housing according to the present invention.

FIG. 5 shows views of an inlet portion of an embodiment of a filter device housing according to the present invention, wherein the illustrated inlet portion has one port.

FIG. 6 shows views of an outlet portion of an embodiment of a filter device housing according to the present invention.

Figure 8:
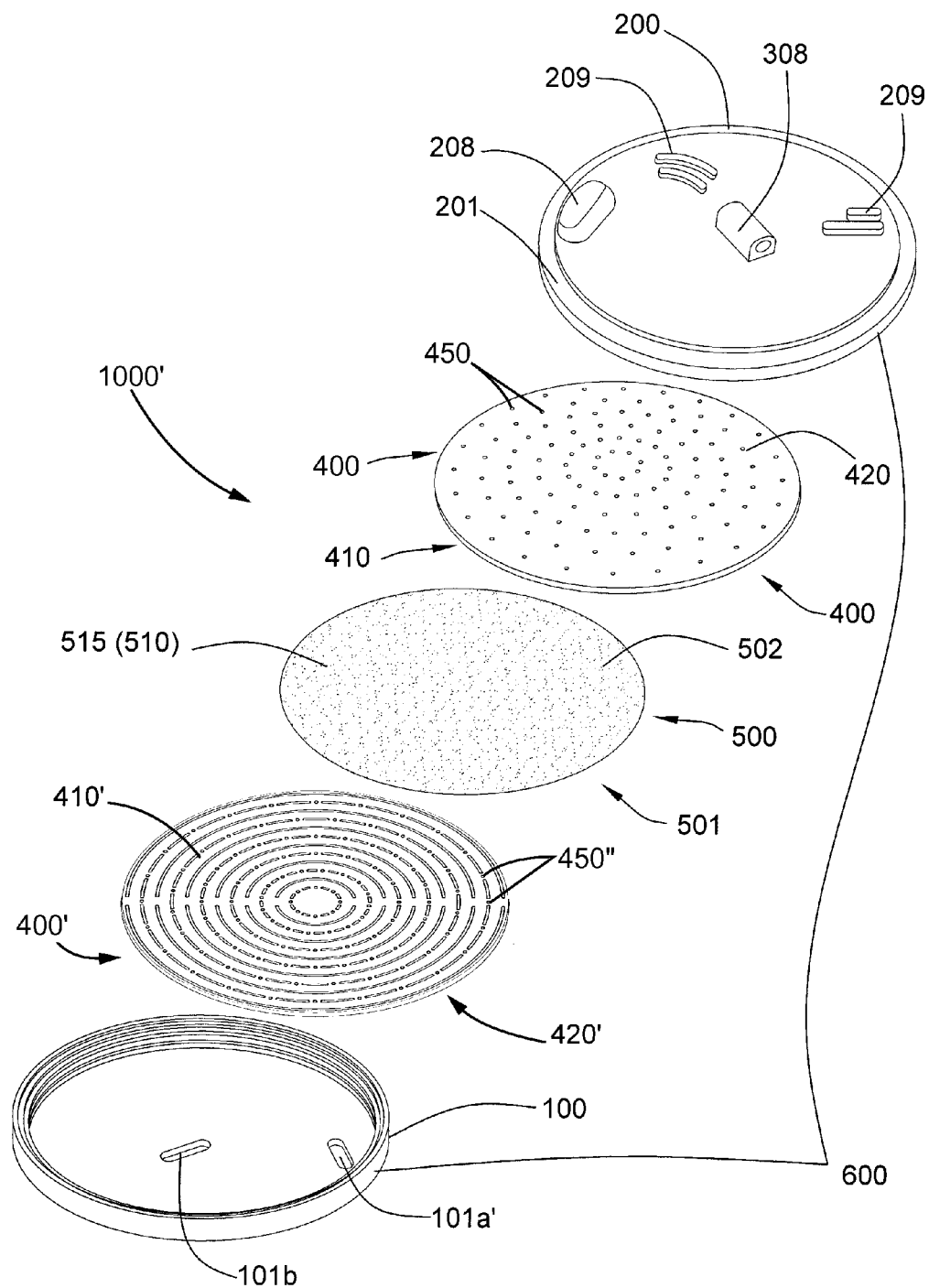

FIG. 8 is an exploded view of an embodiment of a filter device according to the present invention, showing a filter device housing comprising an inlet portion, and an outlet portion, and also a first diffusing plate and a second diffusing plate, and a leukocyte depletion filter interposed between the first diffusing plate and the second diffusing plate, in this illustrated filter device, the inlet portion and the outlet portion each have two ports, wherein the inlet portion includes an inlet port and an elution fluid outlet port, and the outlet portion includes an outlet port and an elution fluid inlet port.

Figure 1:
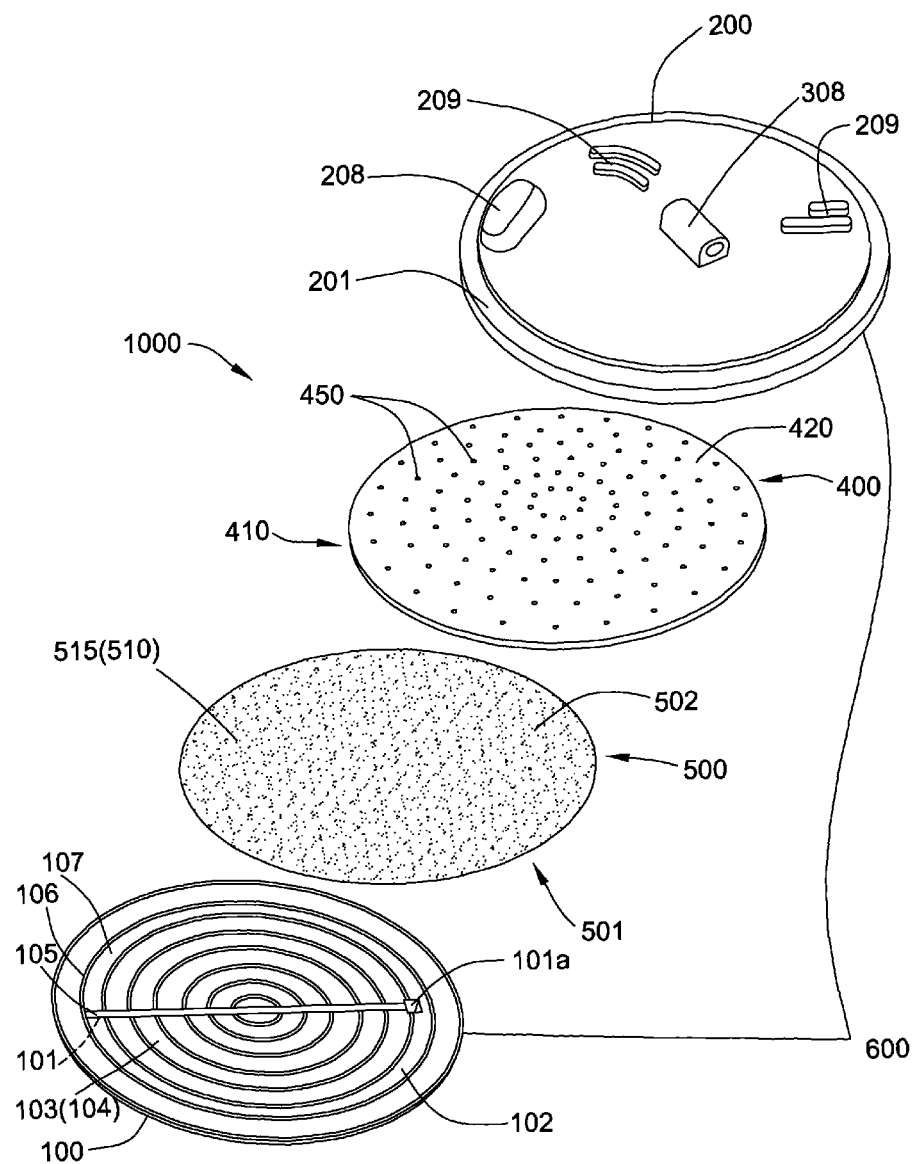
FIG. 1 is an exploded view of an embodiment of a filter device according to the present invention, showing a filter device housing comprising an inlet portion and an inlet port, and an outlet portion comprising an outlet port and an elution fluid inlet port, and also showing a leukocyte depletion filter and a diffusing plate between the inlet and outlet portions.
Figure 9:
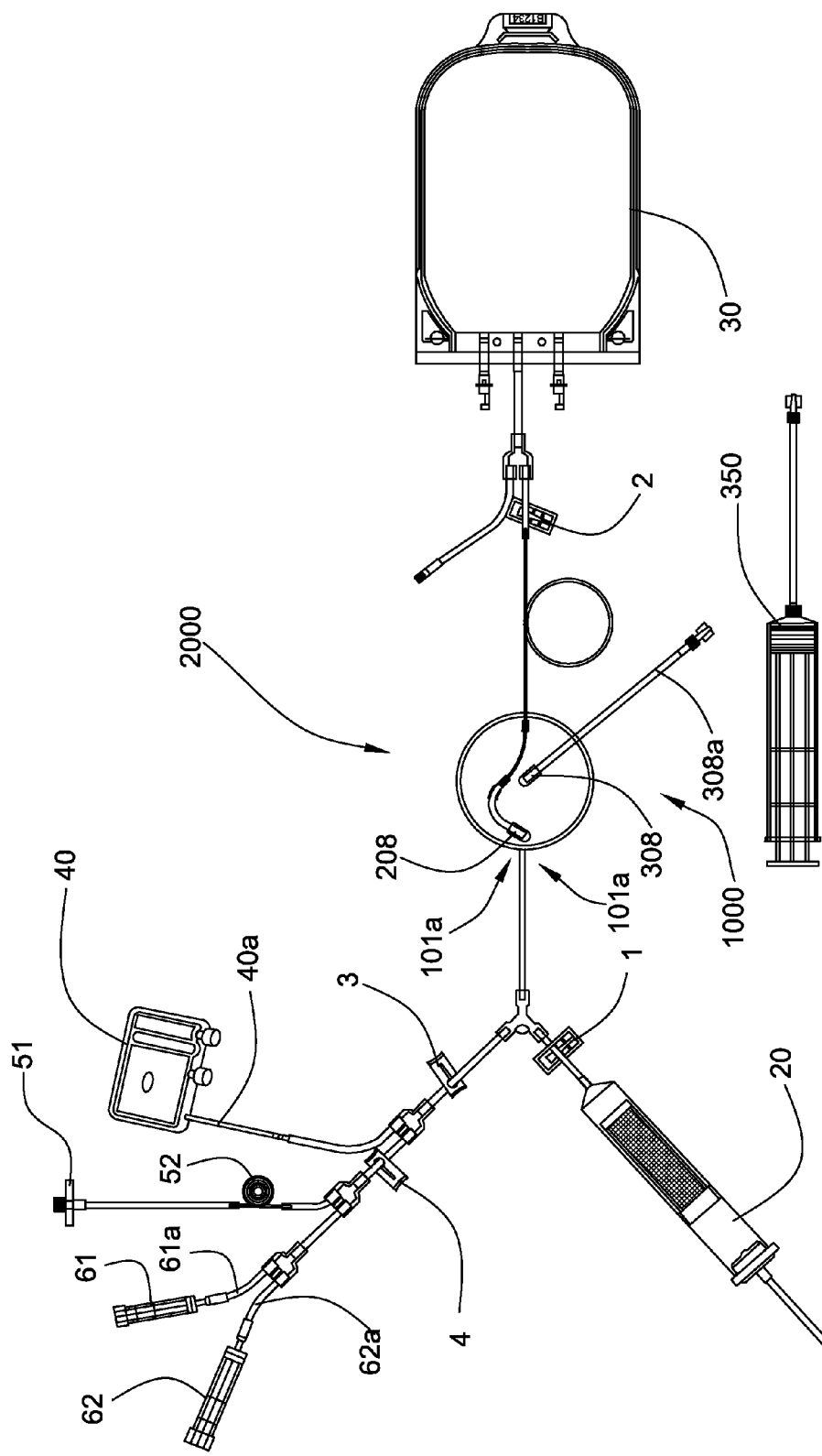

FIG. 9 shows an embodiment of an illustrative system according to the invention, the illustrated system including the embodiment of the filter device shown in FIG. 1.

Figure 10:
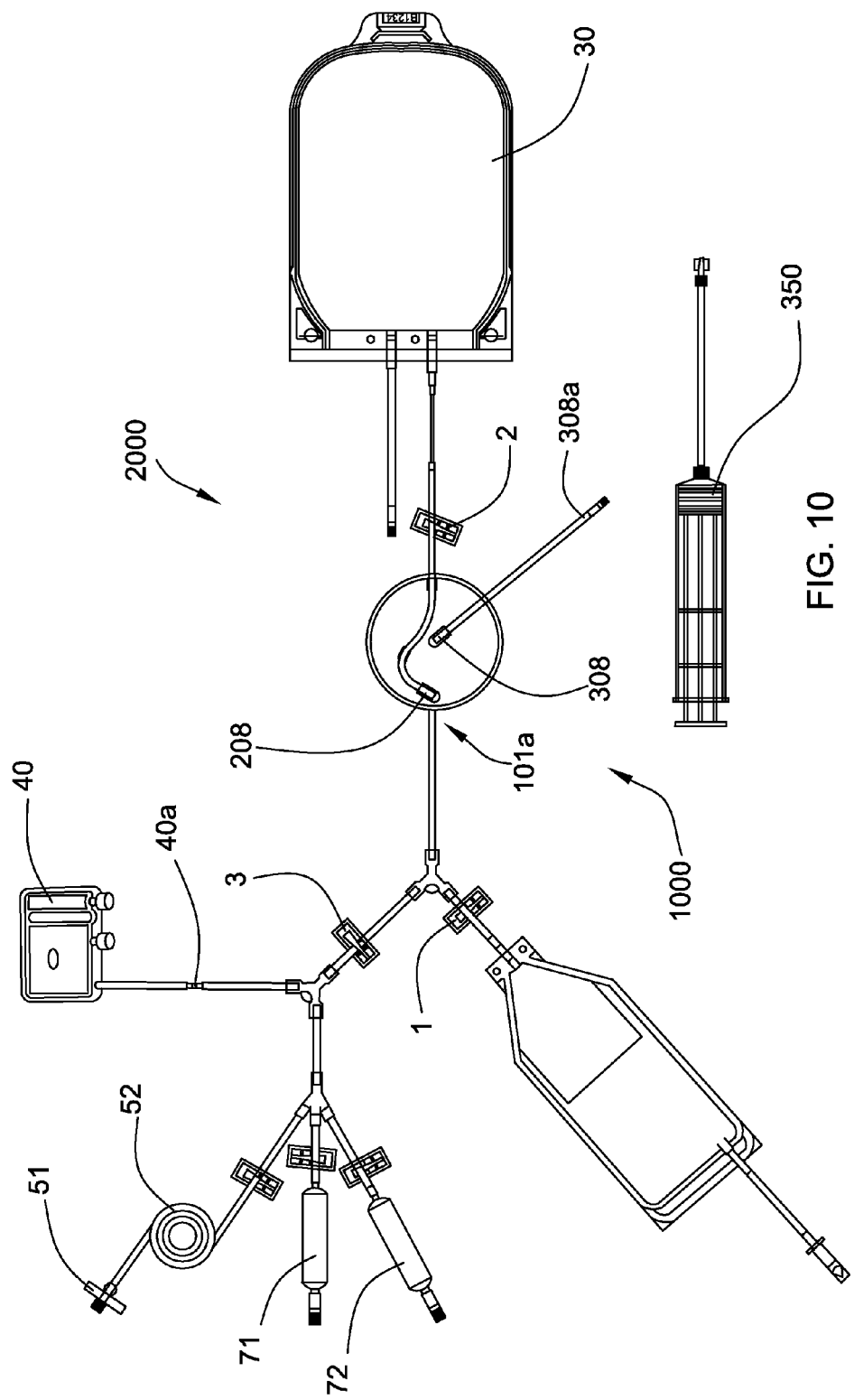

FIG. 10 shows another embodiment of an illustrative system according to the invention, the illustrated system including the embodiment of the filter device shown in FIG. 1.

Figure 11:
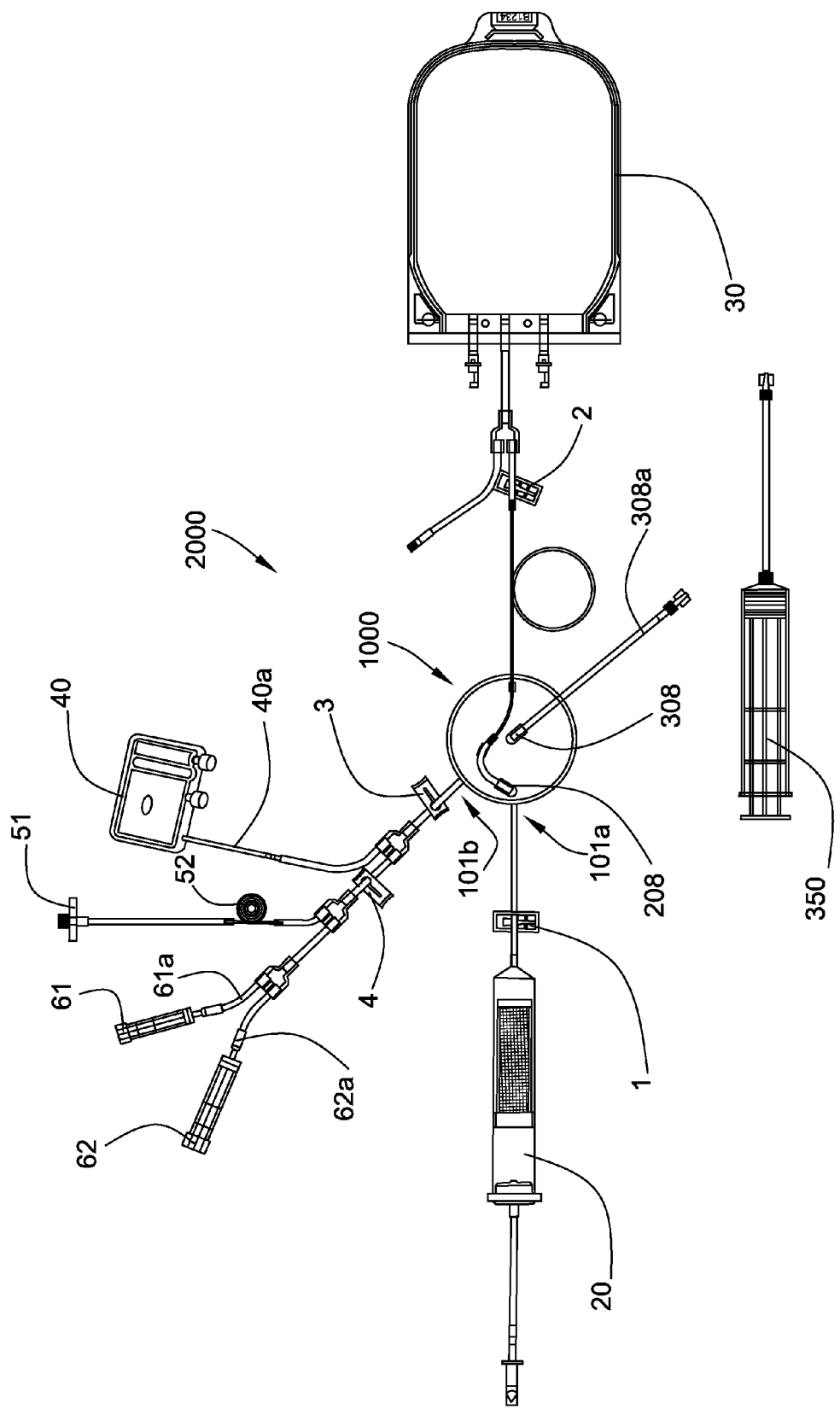

FIG. 11 shows yet another embodiment of an illustrative system according to the invention, the illustrated system including the embodiment of the filter device shown in FIG. 8.

Figure 12:
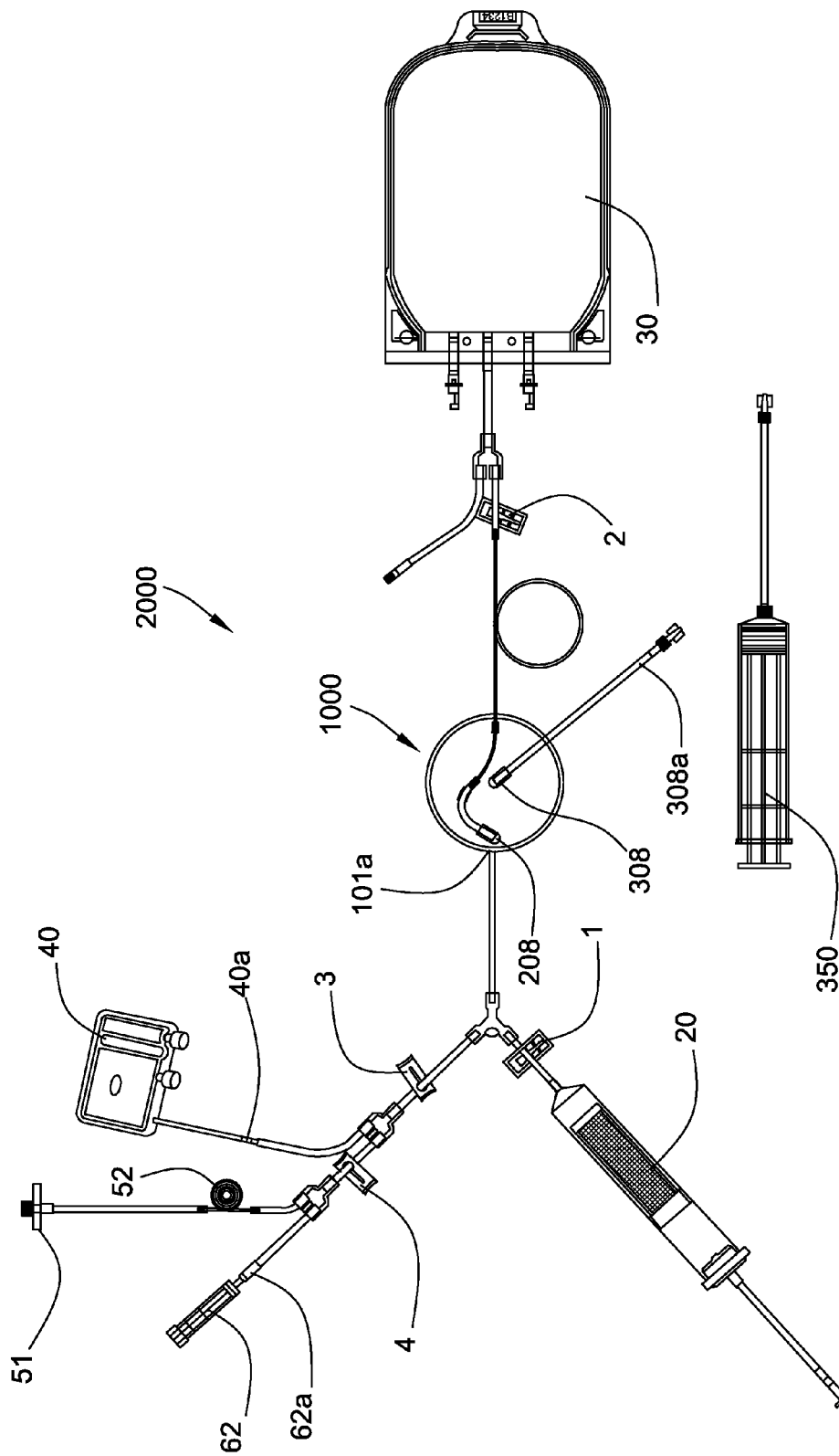

FIG. 12 shows yet another embodiment of an illustrative system according to the invention, the illustrated system including the embodiment of the filter device shown in FIG. 1.

Figure 13:
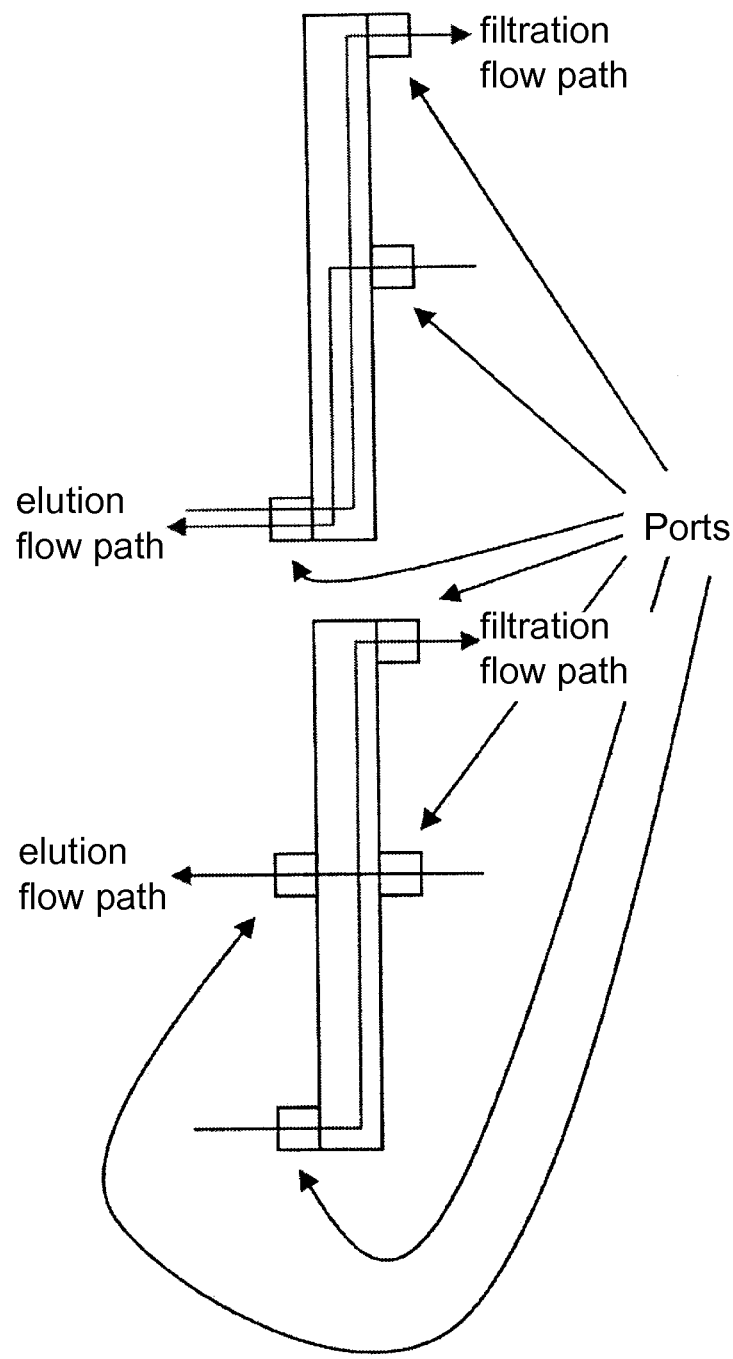

FIG. 13 shows, diagrammatically, fluid flow paths for embodiments of filter devices according to the invention, wherein the filter devices comprise one or two diffusing plates, and wherein the inlet portions and/or the outlet portions of the filter housings comprise one or two ports.

DETAILED DESCRIPTION OF THE INVENTION

Advantageously, the recovery and harvesting of desired biological fluid components, preferably, target cells such as leukocytes and/or stem cells, can be increased using devices according to the invention, and the devices are especially useful in applications involving cord blood, amniotic fluid and/or bone marrow.

An embodiment of the invention provides a biological fluid processing device comprising (a) a housing comprising an inlet portion including one or more ports, an outlet portion including one or more ports, and defining at least one fluid flow path between an inlet portion port and an outlet portion port, (b) a porous filter having a first surface and a second surface, disposed in the housing across the fluid flow path; and (c) a first perforated diffusing plate having a first surface and a second surface, disposed in the housing across the fluid flow path, wherein the first diffusing plate is disposed in the housing between the second surface of the porous filter and the outlet portion port(s). Preferably, the outlet portion includes a first port comprising an outlet port, and a second port comprising an elution fluid inlet port, and the housing defines a first fluid flow path between an inlet portion port and the outlet port, and a second fluid flow path between an inlet portion port and the elution fluid inlet port. In an embodiment, the inlet portion includes a first port comprising an inlet port, and a second port comprising an elution fluid outlet port, and the housing defines a first fluid flow path between the inlet portion inlet port and the outlet portion outlet port, and a second fluid flow path between the outlet portion elution fluid inlet port and the inlet portion elution fluid inlet port.

In some embodiments, the biological fluid processing device further comprises a second perforated diffusing plate having a first surface and a second surface, disposed in the housing across the fluid flow path(s), wherein the second diffusing plate is disposed in the housing between the first surface of the porous filter and the inlet portion port(s).

Preferably, the porous filter comprises at least one porous leukocyte depletion medium.

Another embodiment of the invention provides a biological fluid processing device comprising (a) a housing comprising an inlet portion including an inlet port, an outlet portion including an outlet port and an elution fluid inlet port, and defining a fluid flow path between the inlet portion inlet port and the outlet portion outlet port, and a fluid flow path between the outlet portion elution fluid inlet port and the inlet portion inlet port; (b) a porous filter having a first surface and a second surface, disposed in the housing across the fluid flow paths; and (c) a first perforated diffusing plate having a first surface and a second surface, disposed in the housing across the fluid flow paths, wherein the diffusing plate is disposed in the housing between the second surface of the porous filter and the outlet portion ports.

Yet another embodiment of the invention provides a biological fluid processing device comprising (a) a housing comprising an inlet portion including at least an inlet port, an outlet portion including an outlet port and an elution fluid inlet port, and defining a fluid flow path between the inlet portion inlet port and the outlet portion outlet port, and a fluid flow path between the outlet portion elution fluid inlet port and an inlet portion port; (b) a porous filter having a first surface and a second surface, disposed in the housing across the fluid flow paths; (c) a first perforated diffusing plate having a first surface and a second surface, disposed in the housing across the fluid flow paths, wherein the diffusing plate is disposed in the housing between the second surface of the porous filter and the outlet portion ports; and (d) a second perforated diffusing plate having a first surface and a second surface, disposed in the housing across the fluid flow paths, wherein the diffusing plate is disposed in the housing between the first surface of the porous filter and the inlet portion ports. In some embodiments of the device, the inlet portion includes an inlet port and an elution fluid outlet port, and the housing defines a fluid flow path between the inlet portion inlet port and the outlet portion outlet port, and a fluid flow path between the outlet portion elution fluid inlet port and an inlet portion elution fluid outlet port; wherein the porous filter, and first perforated diffusing plate, and the optional second perforated diffusing plate, are disposed in the housing across the fluid flow paths.

In some embodiments of the device, at least one perforated diffusing plate comprises perforations arranged in a pattern of two or more generally concentric circles and/or the perforated diffusing plate comprises perforations arranged in a non-concentric pattern. Alternatively, or additionally, the first surface of at least one perforated diffusing plate includes upwardly protruding ridges, and the first surface of the perforated diffusing plate can include a plurality of upwardly protruding concentric ridges. In some embodiments, the ridges are non-continuous, and alternating rows of ridges are interrupted by perforations.

In another embodiment, a method for obtaining one or more desired biological fluid components comprises (a) passing a biological fluid through an embodiment of the biological fluid filter device, wherein the fluid passes from an inlet portion port through an outlet portion port, wherein one or more desired biological fluid components are retained by the filter as the fluid passes along a fluid flow path from an inlet portion port through an outlet portion port; b) passing an elution fluid along a fluid flow path from an outlet portion elution fluid inlet port through the first diffusing plate, the filter, and an inlet portion port, wherein the elution fluid elutes one or more desired biological fluid components from the filter; and, obtaining one or more of the eluted desired biological fluid components.

In an embodiment of the method wherein the biological fluid filter device further comprises a second diffusing plate, a method for obtaining one or more desired biological fluid components comprises (a) passing a biological fluid through an embodiment of the biological fluid filter device, wherein the fluid passes from an inlet portion port through an outlet portion port, wherein one or more desired biological fluid components are retained by the filter as the fluid passes along a fluid flow path from an inlet portion port through an outlet portion port; b) passing an elution fluid along a fluid flow path from an outlet portion elution fluid inlet port through the first diffusing plate, the filter, the second diffusing plate, and an inlet portion port, wherein the elution fluid elutes one or more desired biological fluid components from the filter; and, obtaining one or more of the eluted desired biological fluid components.

In some embodiments, the method can be carried out while maintaining a closed system. Preferably, the elution fluid elutes leukocytes and/or stem cells from the filter, and the method includes obtaining eluted leukocytes and/or stem cells. In some embodiments of the method, the eluted leukocytes and/or stem cells are further processed, e.g., to subsequently obtain more purified cells. Additionally, or alternatively, eluted biological fluid components, preferably leukocytes and/or stem cells, are cryopreserved.

In another embodiment, a system for processing biological fluid is provided, comprising an embodiment of the biological fluid processing device, and a plurality of containers, and an elution fluid delivery device.

Another embodiment of a biological fluid processing system comprises an embodiment of the biological fluid processing device, in fluid communication with at least one container, more preferably, at least two containers. In one embodiment of the system, one of the containers comprises a container suitable for cryopreservation of stem cells and/or leukocytes. In some embodiments, the system further comprises an elution fluid delivery device.

The invention can be carried out using biological fluid from a variety of sources, particularly mammals. It is preferred that the mammals are from the order Carnivora, including Felines (cats) and Canines (dogs), the order Artiodactyla, including Bovines (cows) and Swims (pigs) or of the order Perssodactyla, including Equines (horses). Typically, the mammals are of the order Primates, Ceboids, or Simoids (monkeys) or of the order Anthropoids (humans and apes). An especially preferred mammal is the human.

Each of the components of the invention will now be described in more detail below, wherein like components have like reference numbers.

In the illustrated embodiment shown in FIGS. 1, 2, and 4-6, the biological fluid processing device 1000 comprises a housing 600 comprising an inlet portion 100 including an inlet 101, an inlet port 101*a* (in this illustrated embodiment, the inlet port 101*a* also comprises an elution fluid outlet port), an optional inlet channel 107 communicating with the inlet port 101*a*, an inlet chamber 102, and an inlet portion wall 103 having an inner surface 104, and an outlet portion 200 comprising an outlet 208, an outlet port 201*a*, an optional outlet channel 207 communicating with the outlet port, an outlet chamber 202, an outlet portion wall 203, an elution fluid inlet port 300, and an optional outlet channel 307 communicating with the elution fluid inlet port, and defining a fluid flow path between the inlet portion inlet port 101*a* and the outlet portion outlet port 201*a*, and defining a fluid flow path between the outlet portion elution fluid inlet port 300 and the inlet portion inlet port 101*a*. For convenience, ports 201*a* and 300 are identified above as outlet portion "outlet port" and "elution fluid inlet port" respectively; however, it should be clear (e.g., as diagrammed in FIG. 13) that, for example, port 201*a* can comprise the outlet portion "elution fluid inlet port" and port 300 can comprise the outlet portion "outlet port" (and this is similarly applicable to the associated structures such as 207, 208, 307 and 308).

The above-referenced illustrated embodiment of the device further comprises a first perforated diffusing plate 400 comprising a first surface 410 and a second surface 420, and perforations 450; and a leukocyte depletion filter 500, comprising a first surface 501 and a second surface 502, the illustrated filter comprising a fibrous leukocyte depletion filter element 515 comprising a fibrous leukocyte depletion medium 510, and the diffusing plate and leukocyte depletion filter are disposed in the housing across the fluid flow paths.

In the illustrated embodiment of the plate 400 in FIGS. 1, 2, and 4, the first surface 410 facing the leukocyte depletion filter has generally planar appearance, and the second surface 420 facing the housing outlet portion ports has a generally convex appearance (e.g., gradually decreasing in thickness from the center to the periphery). However, other arrangements can be utilized, and in those embodiments including first and second plates, the two plates can be arranged differently.

Figure 3A:
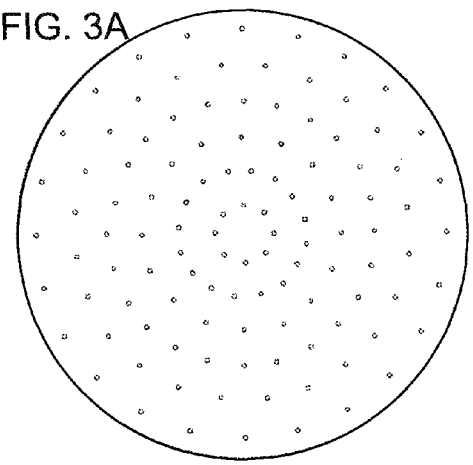
FIG. 3 shows a variety of illustrative diffusing plate perforation patterns and distributions (A-N).
Figure 3D:
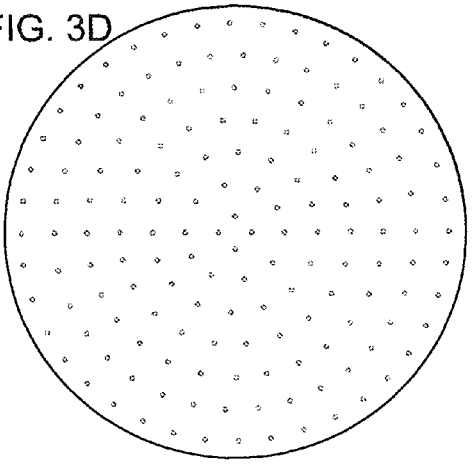
Figure 3B:
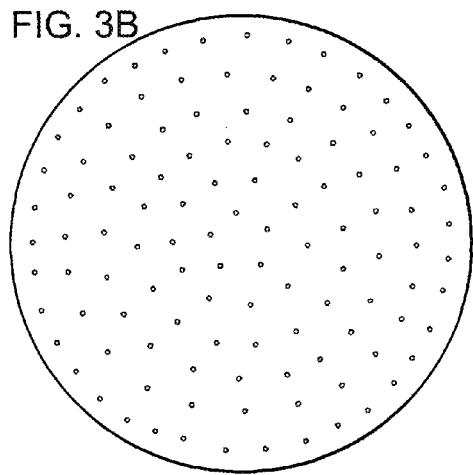
Figure 3E:
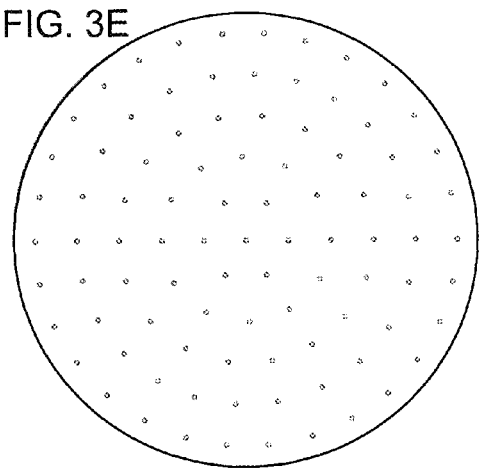
Figure 3C:
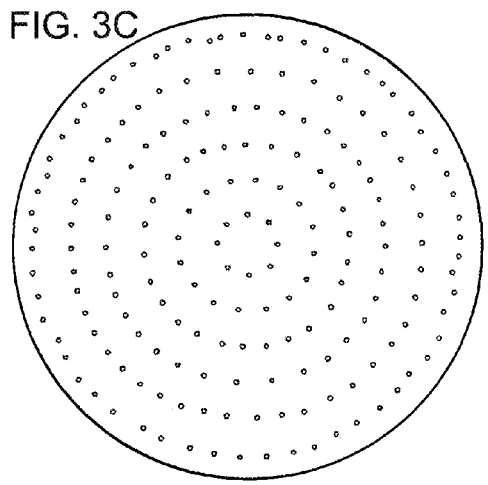
Figure 3F:
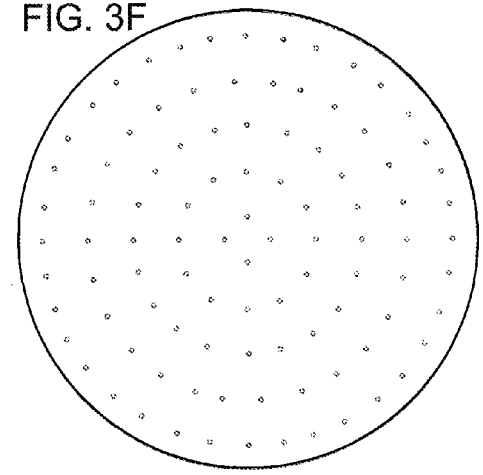
Figure 3G:
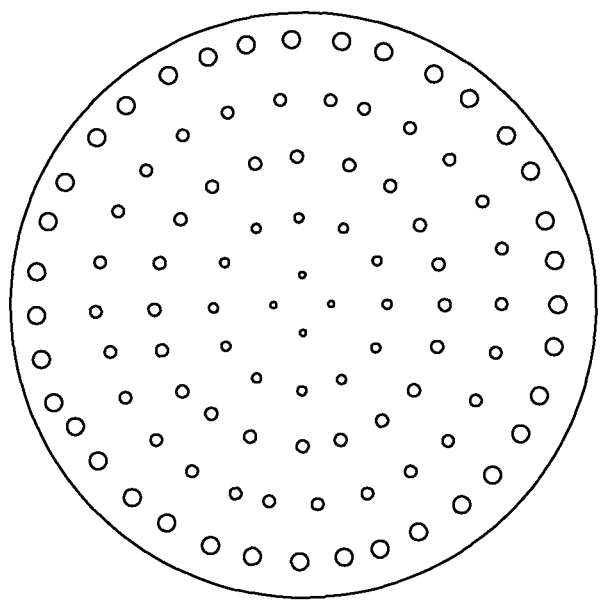
Figure 3H:
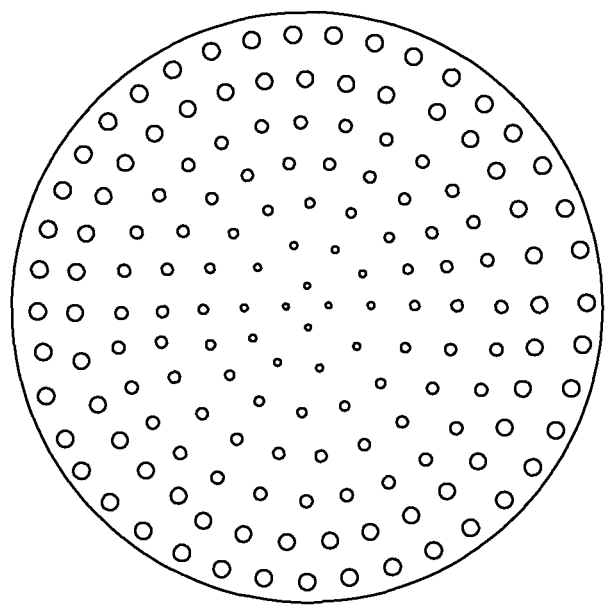
Figure 3I:
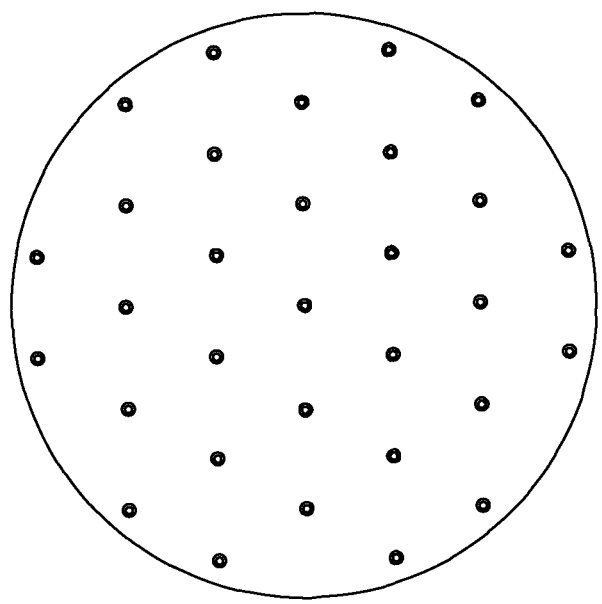
Figure 3J:
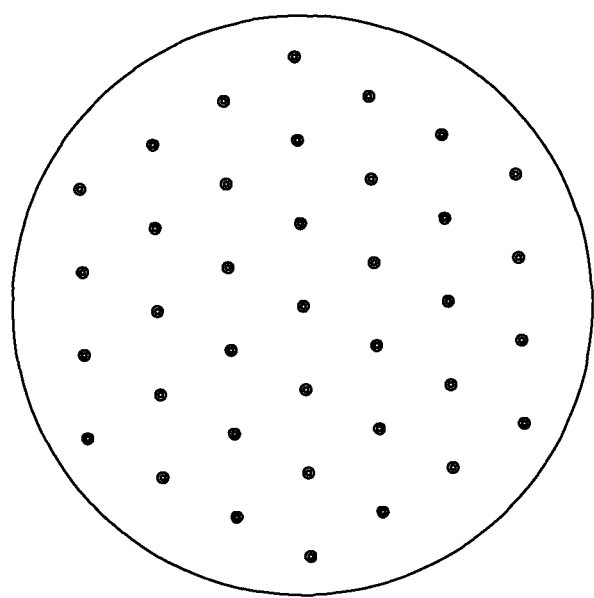
Figure 3K:
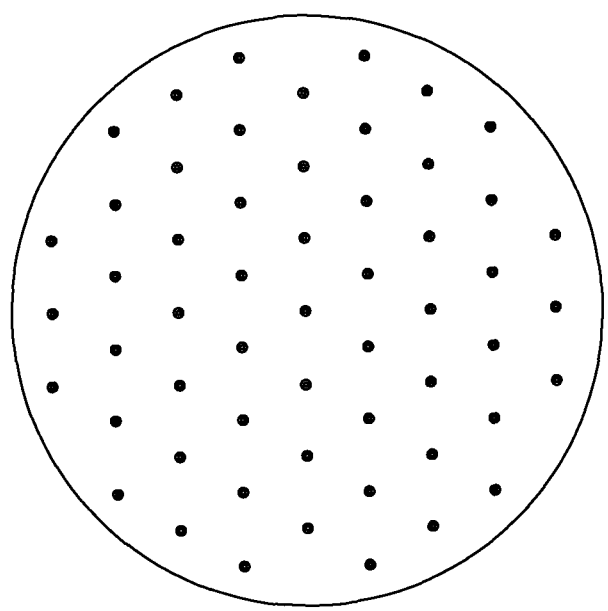
Figure 3L:
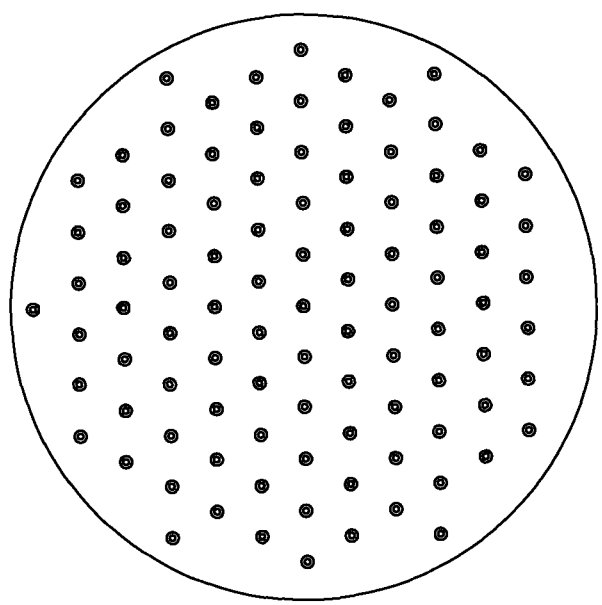
Figure 3M:
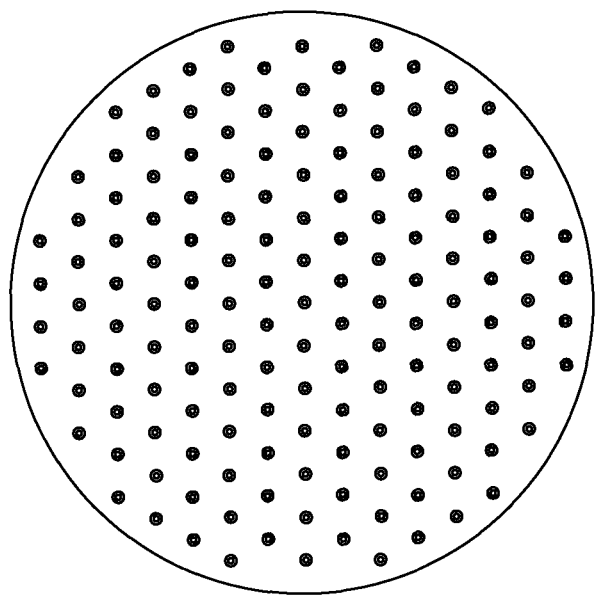
Figure 3N:
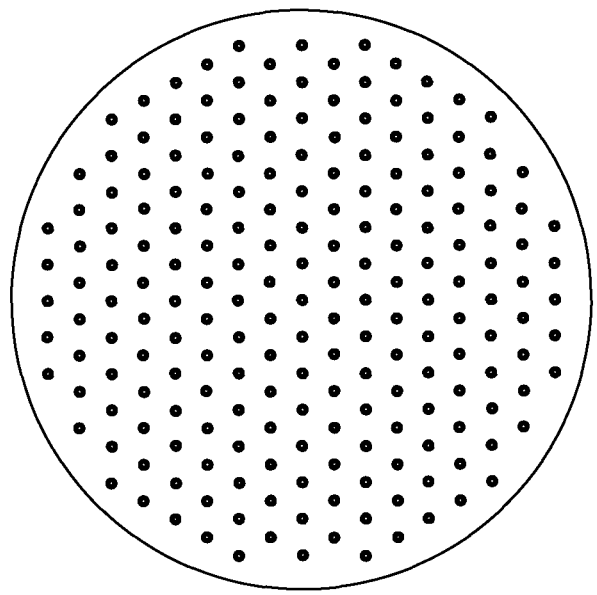

The perforations can be in any suitable pattern and distribution (e.g., illustrative patterns and distributions are shown in FIGS. 3A-3N), and in those embodiments including first and second plates, the two plates can have different patterns and/or distributions. Preferably, the perforations are arranged to direct elution fluid through as much of the filter medium as possible, while reducing elution fluid flow overlap through adjacent perforations, while the device (including the diffusing plate) provides a threshold of force of at least about 10 psig, preferably, at least about 15 psig, more preferably, at least about 20 psig. In some embodiments, the threshold of force is in the range of about 20 psig to about 45 psig.

In some embodiment wherein the plate is circular, a plurality of perforations form a pattern of two or more (e.g., 3, 4, 5, 6, 7, 8, or more) generally concentric circles wherein the circles (formed by a plurality of perforations generally equidistant from the center of the plate) increase in diameter from the center toward the outer periphery of the plate. In some other embodiments, the plurality of perforations do not form generally concentric circles, or the patterns include a combination of generally concentric circles and non-circular patterns. In some of the illustrated embodiments, the perforations toward the outer periphery form generally concentric circles, wherein in some embodiments the perforations in and/or near the center form a generally concentric circle (e.g., as illustrated in FIGS. 3A and 3C), and in some other embodiments, the central pattern differs from the pattern of the rest of the plate, e.g., the central pattern is not generally concentric (for example, as illustrated in FIGS. 3B, 3D, and 3F), or the plate can have few perforations in the center (e.g., FIG. 3E has a single perforation in the center).

In embodiments illustrated in FIGS. 3A and 3C, the perforations form a pattern of six generally concentric circles wherein the circles increase in diameter from the center toward the outer periphery of the plate. In some other illustrated embodiments (FIGS. 3B, and 3D-3H), the non-central part of the plate has generally concentric circles wherein the circles increase in diameter from the center toward the outer periphery of the plate. In some other illustrated embodiments (FIGS. 3I-3N), the perforations form different patterns (e.g., non-circular), and, for example, the perforations near the outer periphery of the plate have a different pattern (e.g., non-circular, with spaces between some of the perforations), than the perforations located at other portions of the plate.

The perforations can have any suitable inside diameter, and the plate can have perforations of different diameter, e.g., wherein the diameters of the perforations in at least one portion (for example, an outer ring) differ from the diameters of the perforations in at least one other portion (for example, a more central ring). Illustratively, a more outer ring can have perforations having a larger average diameter than the average diameters of the perforations in a more central portion (e.g., as shown in FIGS. 3G and 3H), or vice versa. Typically, the average inside diameters of the individual perforations are in the range of from about 0.005 inches (about 0.1 mm), or less, to about 0.12 inches (about 3.0 mm), or more. The perforations can have substantially the same inner diameter from one surface to another, or, in the embodiment shown in the cross-sectional view of FIG. 2, the perforations can provide asymmetric openings, e.g., the perforations at the surface 420 have a larger internal diameter than the perforations at the surface 410. Alternatively, the perforations at the surface 410 can have a larger internal diameter than the perforations at the surface 420 (not shown). In those embodiments including first and second plates, the two plates can have different diameter perforations and/or opening symmetries.

Either or both surfaces of a plate can further include additional components, for example, ridges. Preferably, the first surface 410 of the plate facing the second surface 502 of the filter includes upwardly protruding ridges, e.g., to space the surfaces apart to improve the drainage of biological fluid from the filter during filtration. In the illustrated embodiment shown in FIG. 2, the surface 410 includes a plurality of concentric ridges 411, wherein the ridges are non-continuous, and alternating rows of ridges are interrupted by perforations 450. In the illustrated embodiment, the ridges form a pattern of twelve generally concentric circles wherein the circles increase in diameter from the center toward the outer periphery of the plate. In those embodiments including first and second plates, the two plates can have different additional components such as ridges and/or arrangements of the components.

A diffusing plate, which is typically an integral, one-piece solid plate having perforations therein, can be any suitable shape, e.g., generally rectangular, square, circular, oval, or triangular. Typically, the shape(s) of the plate(s) will generally correspond to that of the interior of the housing, e.g., for ease of fitting and/or sealing in the housing. For example, in the illustrated embodiments, the housing and plate(s) are generally circular.

The housing can include a variety of configurations including any number of ports, and any location of ports, and providing flow paths between an inlet portion port and an outlet portion port, wherein the first diffusing plate and leukocyte depletion filter (and the optional second diffusing plate) are disposed in the housing across the fluid flow paths. In the illustrated embodiments, the inlet portion includes one or two ports, and the outlet portion includes two ports. However, the outlet portion can include one port, and the inlet portion and/or outlet portion can have 3 or more ports.

In one preferred embodiment, the elution fluid inlet port is in the outlet portion wall and located opposing and approximately central to the second surface of the first diffusion plate, the outlet portion outlet port is in the outlet portion wall and located opposing but not central to the second surface of the first plate, and the inlet portion inlet port is in the inlet portion wall and located opposing but not central to the first surface of the filter.

If desired, the device can include one or more spacer and/or drainage components, as separate elements (such as, for example, mesh elements) and/or as part of the housing (such as one or more ridges on the surfaces of the housing facing the upstream and/or downstream surfaces of the filter). Such components may improve the flow of fluid through the filter device, e.g., for priming and/or for passing the biological fluid from the inlet port through the filter and the outlet port, and/or for passing the elution fluid from the elution port through the filter and the inlet port.

In the illustrated embodiment shown in FIG. 5, the inlet portion 100 includes an inlet portion wall 103 including an inner surface 104, including a slot 105, and a plurality of concentric ridges 106 and channels 107, wherein the ridges and channels are interrupted by the slot. In this illustrated embodiment, the slot varies in depth, having a greater depth at the end near the inlet portion inlet port 101a, than at the other end of the slot. The illustrated inlet portion also includes an inlet tube 108, leading to the inlet portion inlet port 101a. The presence of ridges provides spacing between the inlet portion wall 103 and the first surface 501 of the filter, and may improve the flow of fluid through the filter device, e.g., for priming and/or for passing the elution fluid from the elution port through the filter and the inlet port.

In the illustrated embodiment shown in FIG. 6, the outlet portion 200 includes an outlet portion wall 203 including an inner surface 204. Typically, as shown in FIG. 4, the appearance of the inner surface 204 is generally complementary to the appearance of the second surface 420 of the plate 400, e.g., when the second surface 420 has a generally convex appearance, the inner surface 204 preferably has a generally concave appearance, and when the second surface 420 is generally planar, the inner surface 204 is generally planar.

Additionally, in the embodiment illustrated in FIG. 6, the outlet portion includes an outlet 208 leading to the outlet portion outlet port 201a, and an elution tube 308 leading to the outlet portion elution fluid inlet port 300, as well as retainers 209 for retaining flexible conduits communicating with at least one of the tubes.

Figure 7:
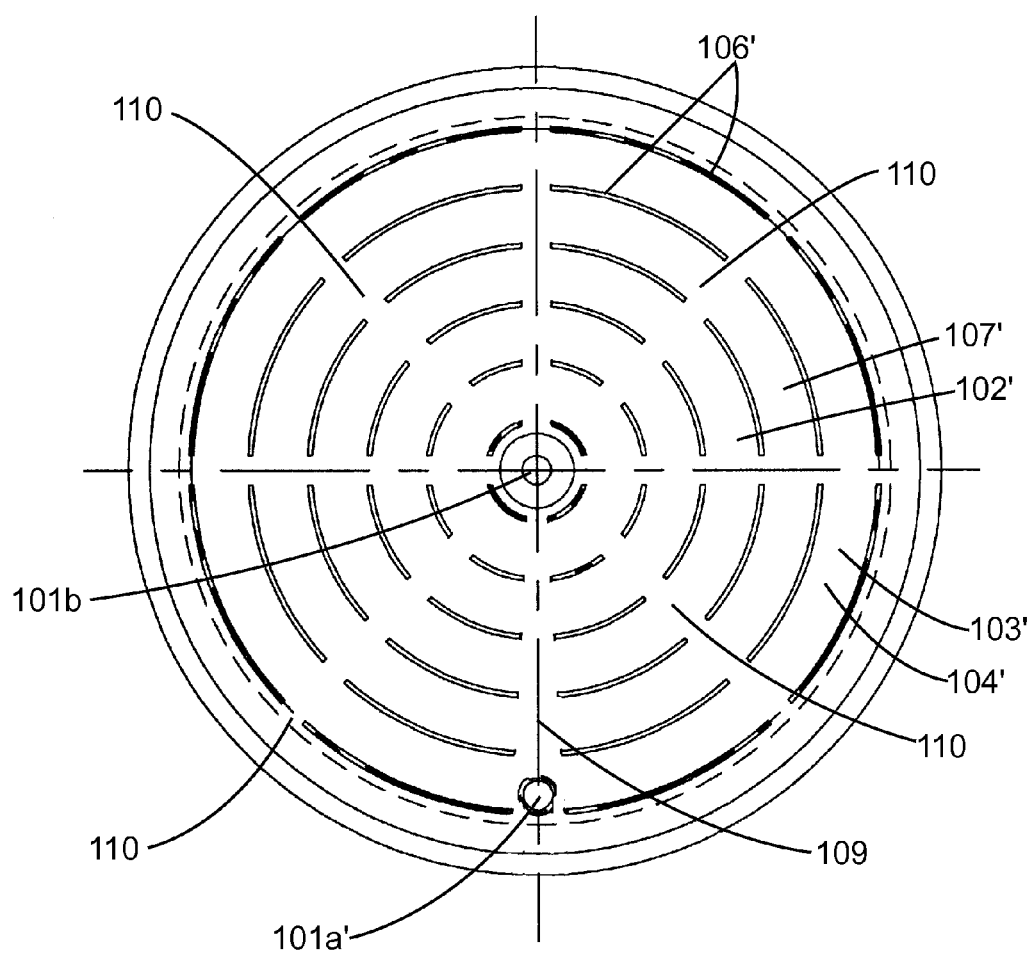
FIG. 7 shows an inside view of an inlet portion of another embodiment of a filter device according to the invention, wherein the illustrated inlet portion includes an inlet port and an elution fluid outlet port.

In the illustrated embodiment shown in FIGS. 7 (inside view of inlet portion) and 8 (filter device), the biological fluid processing device 1000' comprises a housing 600' comprising an inlet portion 100' including an inlet 101', an inlet port 101a,' an elution fluid outlet port 101b, an optional inlet channel 107 communicating with the inlet port 101a', an optional channel 109 communicating with ports 101a' and 101b, an inlet chamber 102', and an inlet portion wall 103' having an inner surface 104', and a plurality of concentric ridges 106' (illustrated as non-continuous ridges) and channels 107', wherein the ridges and channels are interrupted by slots 110, and an outlet portion 200 comprising an outlet 208, an outlet port 201a, an optional outlet channel 207 communicating with the outlet port, an outlet chamber 202, an outlet portion wall 203, an elution fluid inlet port 300, and an optional outlet channel 307 communicating with the elution fluid inlet port, and defining a fluid flow path between the inlet portion inlet port and the outlet portion outlet port, and defining a fluid flow path between the outlet portion elution fluid inlet port and the inlet portion inlet port. The illustrated embodiment of the device further comprises a first perforated diffusing plate 400 comprising a first surface 410 and a second surface 420, and perforations 450; a leukocyte depletion filter 500, comprising a first surface 501 and a second surface 502, the illustrated filter comprising a fibrous leukocyte depletion filter element 515 comprising a fibrous leukocyte depletion medium 510, and a second perforated diffusing plate 400' comprising a first surface 410' and a second surface 420', and perforations 450', wherein the leukocyte depletion filter is interposed between the first and second diffusing plates, and the diffusing plates and leukocyte depletion filter are disposed in the housing across the fluid flow paths.

For convenience, ports 101a' and 101b are identified above as inlet portion "inlet port" and "elution fluid outlet port" respectively; however, it should be clear (e.g., as diagrammed in FIG. 13) that, for example, port 101a' can comprise the inlet portion "elution fluid outlet port" and port 101b can comprise the inlet portion "inlet port" (and this is similarly applicable to the associated structures such as 107). As stated above regarding another embodiment, for convenience, ports 201a and 300 are identified above as outlet portion "outlet port" and "elution fluid inlet port" respectively; however, it should be clear (e.g., as diagrammed in FIG. 13) that, for example, port 201a can comprise the outlet portion "elution fluid inlet port" and port 300 can comprise the outlet portion "outlet port" (and this is similarly applicable to the associated structures such as 207, 208, 307 and 308).

In the illustrated embodiment shown in FIG. 7, the surface 410 includes a plurality of concentric ridges 411, wherein the ridges are non-continuous, and alternating rows of ridges are interrupted by perforations 450.

A variety of leukocyte depletion filters are suitable for use in the invention. In the illustrated embodiment, the porous leukocyte depletion filter 500 comprising a first surface 501 and a second surface 502 comprises at least one porous fibrous leukocyte depletion element 515 comprising at least one porous fibrous leukocyte depletion medium 510, wherein the medium can comprise one or more layers of media. The filter can include a plurality of filter elements. The filter can include additional elements, layers, or components, that can have different structures and/or functions, e.g., at least one of prefiltration, support, drainage, spacing and cushioning. Illustratively, the filter can also include at least one additional element such as a mesh and/or a screen.

A variety of biological fluid component elution fluids are suitable for use in the invention. Typically, the elution fluid is physiologically compatible with the desired biological fluid component(s), and does not substantially effect the component(s). Illustrative fluids include, for example, saline (including normal saline and phosphate buffered saline (PBS)), as well as those fluids, including more viscous fluids, disclosed in U.S. Pat. Nos. 6,544,751 and 7,291,450.

The desired components captured or retained by the filter are released by backflushing from the porous filter, e.g., passing the elution fluid from the elution fluid inlet port, through a diffusing plate, and through the porous filter in a direction from the second surface of the filter (for convenience, hereinafter referred to as "the downstream surface") toward the first surface of the filter (for convenience, hereinafter referred to as "the upstream surface"), and through an inlet portion port. In those embodiments including first and second diffusing plates, backflushing comprises passing the elution fluid from the elution fluid inlet port, through a first diffusing plate, and through the porous filter in a direction from the downstream surface of the filter, toward the upstream surface of the filter, through the second diffusing plate, and through an inlet portion port.

The backflushing can be accomplished at any suitable fluid flow rate, e.g., about 0.1-15 L/min/m², although flow rates significantly more or less than this range can be used. For example, backflushing can be accomplished at a fluid flow rate of about 0.5-10 L/min/m², such as about 1-8 L/min/m²; more preferably the flow rate is about 1.5-7 L/min/m², such as about 2-6 L/min/m² or even about 2.5-5 L/min/m² (e.g., about 3-4 L ml/min/m²). The most preferable flow rate may depend upon the viscosity and/or temperature of the elution fluid, and the nature of the filter medium. Thus, in some applications, such as when more gentle treatment is desired, backflushing can be accomplished at a flow rate about 1-100 ml/min/m², (e.g., about 15-85 ml/min/m²); more preferably the flow rate is about 30-70 ml/min/m² or even about 40-60 ml/min/m² (e.g., about 50 ml/min/m²). Additionally, in some embodiments, the flushing can include pulsing the flow of the flushing fluid.

In accordance with embodiments of the invention, any suitable volume of biological fluid can be processed, and the device can include a variety of filters, e.g., filters having diameters in the range from, for example, about 0.5 inches (about 1.2 cm), or less, to about 5 inches (about 12 cm), or more. Thus, for such filters, the elution pressure is typically in the range of from about 1 psi (about 6.89 kPa) to about 100 psi (about 689 kPa); the inner diameter of the perforations is typically in the range of from about 0.005 inches (about 0.12 mm) to about 0.12 inches (about 3.0 mm), the media clearance (elutable area of filter medium) per perforation is in the range of from about 0.010 in² (about 6.45 mm²) to about 1 in² (about 645 mm²); and the elution flow rate is in the range of from about 1 ml/s to about 50 ml/s. Based upon this, the perforations can be easily and quickly arranged to encompass the most area of the filter media.

Embodiments of filter devices can be included in a biological fluid processing system, e.g., a system including a plurality of conduits and containers, preferably flexible containers such as sampling pouches and blood bags (e.g., collection bags and/or satellite bags). In one embodiment, a system according to the invention comprises a closed system. A wide variety of suitable containers and conduits are known in the art. For example, blood collection and satellite bags, sampling pouches, and conduits, can be made from plasticized polyvinyl chloride. Bags, pouches and/or conduits can also be made from, for example, ethylene butyl acrylate copolymer (EBAC) resin, ethylene methyl acrylate copolymer (EMAC) resin, plasticized ultra-high-molecular weight PVC resin, and ethylene vinyl acetate (EVA). The bags, pouches, and/or conduits can also be formed from, for example, polyolefin, polyurethane, polyester, and polycarbonate.

In those embodiments including cryopreservation of the desired biological fluid components (e.g., leukocytes and/or stem cells), suitable additional system components, e.g., containers and conduits compatible with cryopreservatives such as dimethyl sulfoxide (DMSO), and/or compatible with cryopreservation, include, but are not limited to, those disclosed in U.S. Pat. Nos. 6,146,124, and 5,789,147, U.S. Patent Application Publication 2004/0254560, and Canadian Patent Application 2259878.

In one embodiment wherein the system further comprises an elution fluid delivery device, the device comprises a syringe pump, or a syringe, in some embodiments, a prefilled syringe containing elution solution.

Other system components include, for example, filters (e.g., for removing clots and/or debris from biological fluid and/or for providing sterile cryopreservative), syringes, and flow control devices (e.g., clamps and/or in-line devices such as transfer leg closures and/or valves), as is known in the art.

The following definitions are used in accordance with the invention.

Biological Fluid. A biological fluid includes any treated or untreated fluid associated with living organisms, particularly blood, including whole blood, warm or cold blood, cord blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or huffy coat (BC); fluid derived from the placenta and/or the umbilical cord; blood products derived from blood or a blood component or derived from bone marrow; fluid including stem cells; amniotic fluid; red cells separated from plasma and resuspended in physiological fluid or a cryoprotective fluid; and platelets separated from plasma and resuspended in physiological fluid or a cryoprotective fluid. A biological fluid also includes a physiological solution comprising a bone marrow aspirate. The biological fluid may have been treated to remove some of the leukocytes before being processed according to the invention. As used herein, blood product or biological fluid refers to the components described above, and to similar blood products or biological fluids obtained by other means and with similar properties.

A "unit" is the quantity of biological fluid from a donor or derived from one unit of whole blood. It may also refer to the quantity drawn during a single donation. Typically, the volume of a unit varies, the amount differing from patient to patient and from donation to donation. Multiple units of some blood components, particularly platelets and huffy coat, may be pooled or combined, typically by combining four or more units.

As used herein, the term "closed" refers to a system that allows the collection and processing (and, if desired, the manipulation, e.g., separation of portions, separation into components, filtration, storage, and preservation) of biological fluid, e.g., donor blood, blood samples, and/or blood components, without the need to compromise the sterile integrity of the system. A closed system can be as originally made, or result from the connection of system components using what are known as "sterile docking" devices. Illustrative sterile docking devices are disclosed in, for example, U.S. Pat. Nos. 4,507,119, 4,737,214, and 4,913,756.

A variety of materials can be used, including synthetic polymeric materials, to produce the fibrous porous leukocyte depletion media of the filter elements according to the invention. Suitable synthetic polymeric materials include, for example, polybutylene terephthalate (PET), polyethylene, polyethylene terephthalate (PET), polypropylene, polymethylpentene, polyvinylidene fluoride, polysulfone, polyethersulfone, nylon 6, nylon 66, nylon 6T, nylon 612, nylon 11, and nylon 6 copolymers, wherein polyesters, e.g., PET and PET, are more preferred. Typically, the fibrous porous media are prepared from melt-blown fibers. For example, U.S. Pat. Nos. 4,880,548; 4,925,572, 5,152,905, and 6,074,869. disclose leukocyte filters and porous filter elements prepared from melt-blown fibers.

A filter element can have any suitable pore structure, e.g., a pore size (for example, as evidenced by bubble point, or by $K_L$ as described in, for example, U.S. Pat. No. 4,340,479, or evidenced by capillary condensation flow porometry), a pore rating, a pore diameter (e.g., when characterized using the modified OSU F2 test as described in, for example, U.S. Pat. No. 4,925,572), or removal rating that reduces or allows the passage therethrough of one or more materials of interest as the fluid is passed through the element. While it is believed leukocytes are primarily removed by adsorption, they can also be removed by filtration. The pore structure can be selected to remove at least some level of leukocytes, while allowing the passing therethrough of desired components, e.g., at least one of plasma, platelets, and red blood cells. The pore structure used depends on the composition of the fluid to be treated, and the desired effluent level of the treated fluid.

The filter element can have any desired critical wetting surface tension (CWST, as defined in, for example, U.S. Pat. No. 4,925,572). The CWST can be selected as is known in the art, e.g., as additionally disclosed in, for example, U.S. Pat. Nos. 5,152,905, 5,443,743, 5,472,621, and 6,074,869. Typically, the filter element has a CWST of greater than about 53 dynes/cm (about 53×10 N/cm), more typically greater than about 58 dynes/cm (about $58 \times 10^{-5}$ N/cm), and can have a CWST of about 66 dynes/cm (about $66 \times 10^{-5}$ N/cm) or more some embodiments, the element may have a CWST in the range from about 62 dynes/cm to about 115 dynes/cm (about 62 to about $162 \times 10^{-5}$ N/cm), e.g., in the range of about 80 to about 100 dynes/cm (about 80 to about $100 \times 10^{-5}$ N/cm).

The surface characteristics of the element can be modified (e.g., to affect the CWST, to include a surface charge, e.g., a positive or negative charge, and/or to alter the polarity or hydrophilicity of the surface) by wet or dry oxidation, by coating or depositing a polymer on the surface, or by a grafting reaction. Modifications include, e.g., irradiation, a polar or charged monomer, coating and/or curing the surface with a charged polymer, and carrying out chemical modification to attach functional groups on the surface. Grafting reactions may be activated by exposure to an energy source such as gas plasma, vapor plasma, corona discharge, heat, a Van der Graff generator, ultraviolet light, electron beam, or to various other forms of radiation, or by surface etching or deposition using a plasma treatment.

The housing can be sealed as is known in the art, utilizing, for example, an adhesive, a solvent, laser welding, radio frequency sealing, ultrasonic sealing and/or heat sealing. Additionally, or alternatively, the housing can be sealed via injection molding.

The housing and diffusing plate can be any suitable shape, e.g., generally rectangular, square, circular, oval, or triangular. The housing and diffusing plate can be fabricated from any suitable rigid impervious material, including any impervious thermoplastic material, which is compatible with the biological fluid being processed. In a preferred embodiment, the housing and diffusing plate are fabricated from a polymer (the housing and diffusing plates can be fabricated from different polymers), such as an acrylic, polypropylene, polystyrene, or a polycarbonated resin, which may be a transparent or translucent polymer. Such housings and diffusing plates are easily and economically fabricated. In those embodiments wherein the housing is fabricated from a polymer that is transparent or translucent, the housing allows observation of the passage of the biological fluid through the housing.

As noted above, embodiments of the device can be included in biological processing systems according to the invention, and if desired, the biological fluid can be processed while maintaining a closed system. A typical embodiment of a biological processing system according to the invention comprises an embodiment of the biological processing device; a plurality of conduits, connectors, and flow control devices; a container for receiving leukocyte depleted fluid; a container for receiving the eluted cells (e.g., leukocytes and/or stem cells), preferably, wherein the container for receiving the eluted cells comprises a container suitable for use in cryopreservation; and one or more sampling devices such as a syringe and/or pouch for obtaining a sample of the eluted cells (e.g., for testing and/or analyzing cells before administering cells to a subject). In those embodiments including two or more sampling devices, at least two of the devices can have the same volume, or different volumes.

FIGS. 9-12 show illustrative embodiments of systems according to the present invention. Each of the illustrated embodiments of a system 2000 includes a biological fluid processing device 1000 (FIG. 9-11) or 1000' (FIG. 12), a collection container (for receiving leukocyte depleted fluid) 30, a container suitable for use in cryopreservation ("freezing bag") 40. The illustrated embodiments also include an optional elution fluid delivery device 350 (shown as a syringe) and an optional cryopreservative delivery system 50 comprising a sterilizing filter 51 and a conduit 52, wherein the system 50 is arranged to provide a controlled cryopreservative flow rate.

The embodiments of the system shown in FIGS. 9, 11, and 12 include a drip chamber 20 including a coarse filter therein, and the embodiment shown in FIG. 10 includes a flexible transfer bag 21, wherein the drip chamber and bag are suitable for receiving the biological fluid to be processed according to the invention.

The embodiments of the system shown in FIGS. 7-10 include at least one sampling device. The embodiments of systems shown in FIGS. 9 and 11 include syringes 61 and 62, wherein syringe 61 is illustrated as having a smaller volume than syringe 62, and the embodiment of the system shown in FIG. 12 includes a single syringe 61. The embodiment of the system shown in FIG. 10 includes two containers (shown as flexible sampling pouches) 63. The illustrated sampling pouches also include access ports or luer fittings.

Illustrative embodiments of methods using systems according to the invention as discussed in more detail below.

An embodiment of a method for obtaining one or more desired biological fluid components comprises (a) passing a biological fluid through an embodiment of the biological fluid filter device, wherein the fluid passes from an inlet portion port through an outlet portion port, wherein one or more desired biological fluid components are retained by the filter as the fluid passes along a fluid flow path from an inlet portion port through an outlet portion port; b) passing an elution fluid along a fluid flow path from an outlet portion elution fluid inlet port through the first diffusing plate, the filter, and an inlet portion port, wherein the elution fluid elutes one or more desired biological fluid components from the filter; and, obtaining one or more of the eluted desired biological fluid components.

In an embodiment of the method wherein the biological fluid filter device further comprises a second diffusing plate, a method for obtaining one or more desired biological fluid components comprises (a) passing a biological fluid through an embodiment of the biological fluid filter device, wherein the fluid passes from an inlet portion port through an outlet portion port, wherein one or more desired biological fluid components are retained by the filter as the fluid passes along a fluid flow path from an inlet portion port through an outlet portion port; b) passing an elution fluid along a fluid flow path from an outlet portion elution fluid inlet port through the first diffusing plate, the filter, the second diffusing plate, and an inlet portion port, wherein the elution fluid elutes one or more desired biological fluid components from the filter; and, obtaining one or more of the eluted desired biological fluid components.

In some embodiments, the inlet portion inlet port also comprises an inlet portion elution fluid outlet port, and the method comprises passing a biological fluid from the inlet portion inlet port/elution fluid outlet port through an outlet portion outlet port, wherein one or more desired biological fluid components are retained by the filter as the fluid passes along a fluid flow path from inlet portion poll/elution outlet port through the outlet portion outlet port; b) passing the elution fluid along a fluid flow path from the outlet portion elution fluid inlet port through the first diffusing plate, the filter, the optional second diffusing plate, and the inlet portion inlet port/elution outlet port; wherein the elution fluid elutes one or more desired biological fluid components from the filter; and, one or more of the eluted desired biological fluid components are obtained.

In some other embodiments, the inlet portion comprises an inlet port and a separate elution fluid outlet port and the method comprises passing a biological fluid from the inlet portion inlet port through the outlet portion outlet port, wherein one or more desired biological fluid components are retained by the filter as the fluid passes along a fluid flow path from inlet portion port through the outlet portion outlet port; b) passing the elution fluid along a fluid flow path from the outlet portion elution fluid inlet port through the first diffusing plate, the filter, the optional second diffusing plate, and the inlet portion elution outlet port; wherein the elution fluid elutes one or more desired biological fluid components from the filter; and, one or more of the eluted desired biological fluid components are obtained.

The elution fluid (a biological fluid component elution fluid) elutes one or more biological fluid components from the filter; and, one or more eluted desired biological fluid components are subsequently obtained. A preferred embodiment of the method comprises obtaining eluted leukocytes and/or stem cells. Embodiments of the method can include carrying out the method while maintaining a closed system. In a preferred embodiment of the method, eluted biological fluid components, preferably leukocytes and/or stem cells, are cryopreserved.

Using the illustrative system 2000 shown in FIG. 9 for reference, in one embodiment of the method, the biological fluid to be processed, e.g., a collected cord blood unit having a volume in the range of from about 65 ml to about 250 ml, typically in a source container or a syringe (not shown), is attached to the system, e.g., via a transfer spike, or luer connection, or sterile docking, upstream of the drip chamber 20. If desired, the elution fluid delivery device 350 can be placed in communication with the system (e.g., via the conduit 308a communicating with elution fluid inlet port 308, using, for example, luer connection, or sterile docking) before attaching the container of biological fluid to the system. Flow control devices 1-4 are initially closed.

Flow control devices 1 and 2 are opened, and the biological fluid passes through the drip chamber 20 (and the coarse filter therein) and through the biological fluid filter device 1000 via inlet portion inlet port 101a, and the filtered (leukocyte-depleted) fluid passes via outlet 208 into container 30. After filtration is completed, flow control devices 1 and 2 are closed.

Flow control device 3 is opened, and the elution fluid delivery device 350 (illustrated as a syringe containing elution fluid therein, but alternatively comprising, for example, a syringe pump), is operated, passing elution fluid via conduit 308a through the elution fluid inlet port 308, the diffusing plate (via the perforations from the downstream surface through the upstream surface), the filter (via the downstream surface and the upstream surface), the inlet portion inlet port/elution fluid outlet port 101a, and into the container 40, which is preferably suitable for use in cryopreservation (container 40 will be referred to hereinafter as the "freezing bag"). Desired cells eluted by the elution fluid pass with the fluid into the freezing bag. Once elution is completed, flow control device 3 is closed.

Optionally, at least one sample of the eluted cells is obtained. For example, fluid control device 4 is opened, and, if desired, sampling device 62 is operated (e.g., by depressing the plunger) to displace fluid in the conduit(s) into the freezing bag 40. Flow control devices 1 and 3 can be opened, and the freezing bag can be compressed to drive air from the bag toward drip chamber 20, and flow control device 3 should be closed before liquid passes from the bag 40. Preferably, the conduit associated with flow control device 3 is heat sealed and cut, and the portion of the system including the freezing bag is separated from the portion of the system including the container 30.

If desired, sampling device 61 can be operated to pass a sample (e.g., about 0.5 ml to about 1 ml) into the device, and the conduit 61a leading to the device 61 can be heat sealed and cut.

A cryoprotectant, typically dimethyl sulfoxide (DMSO), is passed from a system/container (if a closed system is to be maintained, a cryoprotectant delivery device system can comprise a prefilled cryoprotectant syringe with a conduit compatible with the cryoprotectant) through a sterilizing filter 51 and conduit 52 into the freezer bag. If desired, sampling device 62 can be operated to displace liquid in the conduit(s) into the freezing bag 40 and (e.g., after mixing the contents in the freezing bag) to withdraw air from the freezing bag and conduit(s).

If a post-cryoprotectant sample is to be taken, sampling device 62 can be operated to pass a sample (e.g., about 0.5 ml to about 1 ml) into the device, and also leave liquid in the conduit 40a for segment preparation. Conduit 62a leading to the device 62 can be heat sealed and cut, and conduit 40a can be heated sealed to provide the desired number of segments.

If a post-cryroprotectant sample is not to be taken, sampling device 62 can be operated to pass liquid from freezing bag 40 in the conduit 40a for segment preparation. Conduit 62a leading to the device 62 can be heat sealed and cut, and conduit 40a can be heated sealed to provide the desired number of segments.

The bag and conduit are frozen and stored (and subsequently further processed) as is known in the art.

Embodiments of methods using the illustrative systems shown in FIGS. 10-12 can be carried out generally similarly to the embodiment of the method using the illustrative system shown in FIG. 9 and described above. However, the biological fluid to be processed, e.g., a collected cord blood unit, typically in a source container or a syringe (not shown), can be attached to the system, e.g., via a transfer spike, or luer connection, or sterile docking, upstream of a transfer container, e.g., transfer container 21 (shown in FIG. 10) rather than a drip chamber. If desired, the transfer container can include a coarse filter therein (not shown).

Additionally, or alternatively, using the illustrative system shown in FIG. 11 for reference (wherein the inlet portion of the biological fluid filter device comprises an inlet port 101a, and an elution fluid outlet port 101b) elution fluid is passed via conduit 308a through the elution fluid inlet port 308, the diffusing plate (via the perforations from the downstream surface through the upstream surface), the filter (via the downstream surface and the upstream surface), the elution fluid outlet port 101b, and into the freezing bag 40.

If samples are desired, samples can be obtained pre- and/or post-cryroprotectant via passing the samples into one or more flexible sampling containers, e.g., flexible sampling pouches (71, 72, as shown in FIG. 10) rather than, for example, syringes.

If, for example, a single sample is obtained, e.g., a pre-cryroprotectant sample, the system can include a single sampling device, e.g., sampling device 62 as shown in FIG. 12, or, for example, a sampling pouch (not shown).

The following examples further illustrate the invention but, of course, should not be construed as in any way limiting its scope.

EXAMPLE 1

This example demonstrates the improved recovery of leukocytes using an embodiment of the device including the diffusing plate according to the invention compared to a device without a diffusing plate.

The device with a diffusing plate provides a minimum threshold of force of about 20 pounds per square inch gauge (PSIG), measured via a gauge connected into the conduit leading to the elution port.

The diffusing plate has a pattern of perforations as generally shown in FIG. 3A. In one set of experiments, the perforations have an average diameter of 0.050 inches, in another set, the perforations have an average diameter of 0.032 inches.

A device is provided as generally shown in FIGS. 1 and 2, wherein the control device does not have a diffusing plate. The leukocyte depletion filter is prepared as generally described in U.S. Pat. No. 4,880,548.

Different volumes of blood are passed through the devices, and the captured cells are eluted using 10% Dextran 40 in saline as the elution fluid, passed through the device via the elution port using a manually operated syringe.

The average recovery of total nucleated cells is about 59% for the control, about 79% for the device with average diameter perforations of 0.050 inches, and about 84% for the device with average diameter perforations of 0.032 inches.

EXAMPLE 2

This example demonstrates the improved recovery of leukocytes using embodiments of the device including one and two diffusing plates according to the invention compared to a device without a diffusing plate.

The devices with diffusing plates provide a minimum threshold of force of about 20 pounds per square inch gauge (PSIG), measured via a gauge connected into the conduit leading to the elution port.

The diffusing plates have patterns of perforations as generally shown in FIG. 3A. In one set of experiments, using a single diffusing plate between the downstream surface of the leukocyte depletion filter and the outlet portion, the perforations have an average diameter of 0.032 inches. In another set, using a first diffusing plate between the downstream surface of the leukocyte depletion filter and the outlet portion, and a second diffusing plate between the upstream surface of the leukocyte depletion filter and the inlet portion, the perforations in the first and second diffusing plates each have an average diameter of 0.030 inches.

Devices are provided as generally shown in FIGS. 1 and 2 (single diffusing plate), and FIG. 8 (first and second diffusing plates), wherein the control device does not have diffusing plates. The leukocyte depletion filter is prepared as generally described in U.S. Pat. No. 4,880,548.

Different volumes of blood are passed through the devices, and the captured cells are eluted using 10% Dextran 40 in saline as the citation fluid, passed through the devices via the elution port using a manually operated syringe.

The average recovery of total nucleated cells is about 59% for the control, about 84% for the device with a single diffusing plate, and about 90% for the device with first and second diffusing plates.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A biological fluid processing device comprising:
   (a) a housing comprising an inlet portion including an inlet portion inlet port, and a separate inlet portion elution fluid outlet port, an outlet portion including an outlet portion outlet port and an outlet portion elution fluid inlet port, and defining a first fluid flow path between the inlet portion inlet port and the outlet portion outlet port and a second fluid flow path between the outlet portion elution fluid inlet port and the inlet portion elution fluid outlet port;
   (b) a porous fibrous leukocyte depletion filter having a first surface and a second surface, disposed in the housing across the first fluid flow path and across the second fluid path; and
   (c) a first perforated diffusing plate having a first surface and a second surface and asymmetrically shaped perforations through the first perforated diffusing plate, the asymmetrically shaped perforations having larger internal diameters at the second surface of the first perforated diffusing plate than at the first surface of the first perforated diffusing plate, the first perforated diffusing plate being disposed in the housing across the first fluid flow path and across the second fluid path, wherein the first perforated diffusing plate is disposed in the housing between the second surface of the porous fibrous leukocyte depletion filter and the outlet portion outlet port and the outlet portion elution fluid inlet port, the first surface of the first diffusing plate facing the second surface of the porous fibrous leukocyte filter.

2. The device of claim 1, wherein the first perforated diffusing plate comprises perforations arranged in a pattern of two or more generally concentric circles.

3. The device of claim 1, wherein the first perforated diffusing plate comprises perforations arranged in a non-concentric pattern.

4. The device of claim 1, wherein the first surface of the first perforated diffusing plate includes upwardly protruding ridges.

5. The device of claim 4, wherein the first surface of the first perforated diffusing plate includes a plurality of upwardly protruding concentric ridges.

6. The device of claim 5, wherein the ridges are non-continuous, and alternating rows of ridges are interrupted by perforations.

7. The device of claim 1, further comprising a second perforated diffusing plate having a first surface and a second surface, disposed in the housing across the first fluid flow path and across the second fluid path, wherein the second perforated diffusing plate is disposed in the housing between the first surface of the porous fibrous leukocyte depletion filter and the inlet portion inlet port and the inlet portion elution fluid outlet port.

8. The device of claim 2, wherein the first perforated diffusing plate comprises perforations arranged in a non-concentric pattern.

9. The device of claim 2, wherein the first surface of the first perforated diffusing plate includes upwardly protruding ridges.

10. The device of claim 3, wherein the first surface of the first perforated diffusing plate includes upwardly protruding ridges.

11. The device of claim 8, wherein the first surface of the first perforated diffusing plate includes upwardly protruding ridges.

12. The device of claim 9, wherein the first surface of the first perforated diffusing plate includes a plurality of upwardly protruding concentric ridges.

13. A method for obtaining one or more biological fluid components, comprising:
   (a) passing a biological fluid through the biological fluid processing device of claim 1, wherein the fluid passes from the inlet portion inlet port of the device through the outlet portion outlet port of the device, wherein one or more desired biological fluid components are retained by the filter as the fluid passes along the first fluid flow path from the inlet portion inlet port through the outlet portion outlet port;
   (b) passing an elution fluid from the outlet portion elution fluid inlet port through the first perforated diffusing plate, the porous fibrous leukocyte depletion filter, and the inlet portion elution fluid outlet port, wherein the elution fluid elutes one or more biological fluid components from the filter; and,
   (c) obtaining one or more eluted biological fluid components.

14. The method of claim 13, comprising obtaining eluted leukocytes and/or stem cells.

15. A method for obtaining one or more biological fluid components, comprising:
   (a) passing a biological fluid through the biological fluid processing device of claim 7, wherein the fluid passes from the inlet portion inlet port of the device through the outlet portion outlet port of the device, wherein one or more desired biological fluid components are retained by the filter as the fluid passes along the first fluid flow path from the inlet portion inlet port through the outlet portion outlet port;
   (b) passing an elution fluid from the outlet portion elution fluid inlet port through the first perforated diffusing plate, the porous fibrous leukocyte depletion filter, the second perforated diffusing plate, and the inlet portion elution fluid outlet port, wherein the elution fluid elutes one or more biological fluid components from the filter; and,
   (c) obtaining one or more eluted biological fluid components.

* * * * *